US010246711B2

United States Patent
Gupte

(10) Patent No.: US 10,246,711 B2
(45) Date of Patent: Apr. 2, 2019

(54) RNAI INHIBITORS OF GLUCOSE-6-PHOSPHATE DEHYDROGENASE FOR TREATING CARDIOVASCULAR AND PULMONARY CONDITIONS

(71) Applicant: Rakhee Gupte, Fishkill, NY (US)

(72) Inventor: Rakhee Gupte, Fishkill, NY (US)

(73) Assignee: Rakhee Gupte, Fishkill, NY (US)

( * ) Notice: Subject to any disclaimer, the term of this patent is extended or adjusted under 35 U.S.C. 154(b) by 0 days.

(21) Appl. No.: 15/813,469

(22) Filed: Nov. 15, 2017

(65) Prior Publication Data
US 2018/0135049 A1 May 17, 2018

Related U.S. Application Data

(60) Provisional application No. 62/422,985, filed on Nov. 16, 2016.

(51) Int. Cl.
| | | |
|---|---|---|
| *C12N 15/11* | (2006.01) | |
| *A61K 48/00* | (2006.01) | |
| *C07H 21/02* | (2006.01) | |
| *C07H 21/04* | (2006.01) | |
| *C12N 15/113* | (2010.01) | |
| *C12Q 1/32* | (2006.01) | |
| *A61K 31/7088* | (2006.01) | |

(52) U.S. Cl.
CPC ........ *C12N 15/113* (2013.01); *A61K 31/7088* (2013.01); *C12Q 1/32* (2013.01); *C12N 2310/14* (2013.01)

(58) Field of Classification Search
CPC .............. C12N 15/113; C12N 15/1135; C12N 2310/531; C12N 15/1137; C12N 2310/14; C12Y 101/01049
See application file for complete search history.

(56) References Cited

U.S. PATENT DOCUMENTS

2005/0032687 A1* 2/2005 Loscalzo .............. A61K 38/443
514/13.3
2010/0317713 A1 12/2010 Olson et al.

FOREIGN PATENT DOCUMENTS

WO WO 2018/093856 5/2018

OTHER PUBLICATIONS

The Mayo Clinic Staff. Strategies to prevent heart disease. Jun. 17, 2016. Downloaded from https://www.mayoclinic.org/diseases-conditions/heart-disease/in-depth/heart-disease-prevention/art-20046502 on Apr. 25, 2018.*
Franziska Baenke, Metabolic dependencies of breast cancer cells, a thesis submitted for the degree of Doctor of Philosophy University College London, Dec. 2012.*
Pellicori et al. (Cardiac Failure Review, 2015, vol. 1:90-95).*

(Continued)

*Primary Examiner* — Terra C Gibbs
(74) *Attorney, Agent, or Firm* — Leason Ellis LLP

(57) ABSTRACT

The present disclosure provides for methods of treating or preventing a cardiovascular disorder and/or a related pulmonary disorder in a subject. In certain embodiments, a therapeutically effective amount of a polynucleotide inhibitor of Glucose-6-phosphate dehydrogenase (G6PD) or a nucleic acid encoding G6PD is administered.

12 Claims, 4 Drawing Sheets
(4 of 4 Drawing Sheet(s) Filed in Color)
Specification includes a Sequence Listing.

(56) References Cited

OTHER PUBLICATIONS

Ryan, John J., et al., "The WHO Classification of Pulmonary Hypertension: A Case-Based Imaging Compendium," Pulmonary Circulation 2.1 (2012): 107-121, PMC, web. Nov. 16, 2016.
Ata H, Rawat DK, Lincoln T, and Gupte SA. Mechanism of glucose-6-phosphate dehydrogenase-mediated regulation of coronary artery contractility. *Am J Physiol Heart Circ Physiol* 300: H2054-2063, 2011.
Cai T, Kuang Y, Zhang C, Zhang Z, Chen L, Li B, Li Y, Wang Y, Yang H, Han Q, and Zhu Y. Glucose-6-phosphate dehydrogenase and NADPH oxidase 4 control STAT3 activity in melanoma cells through a pathway involving reactive oxygen species, c-SRC and SHP2. *Am J Cancer Res* 5: 1610-1620, 2015.
Chettimada S, Gupte R, Rawat D, Gebb SA, McMurtry IF, and Gupte SA. Hypoxia-induced glucose-6-phosphate dehydrogenase overexpression and -activation in pulmonary artery smooth muscle cells: implication in pulmonary hypertension. *American Journal of Physiology Lung Cellular and Molecular Physiology* 308: L287-300, 2015.
Chettimada S, Joshi SR, Alzoubi A, Gebb SA, McMurtry IF, Gupte R, and Gupte SA. Glucose-6-phosphate dehydrogenase plays a critical role in hypoxia-induced CD133+ progenitor cells self-renewal and stimulates their accumulation in the lungs of pulmonary hypertensive rats. *American Journal of Physiology Lung Cellular and Molecular Physiology* 307: L545-556, 2014.
Chettimada S, Rawat DK, Dey N, Kobelja R, Simms Z, Wolin MS, Lincoln TM, and Gupte SA. Glc-6-PD and PKG contribute to hypoxia-induced decrease in smooth muscle cell contractile phenotype proteins in pulmonary artery. *American Journal of Physiology Lung Cellular and Molecular Physiology* 303: L64-74, 2012.
Gupte SA. Glucose-6-phosphate dehydrogenase: a novel therapeutic target in cardiovascular diseases. *Curr Opin Investig Drugs* 9: 993-1000, 2008.
Gupte SA and Wolin MS. Relationships between vascular oxygen sensing mechanisms and hypertensive disease processes. *Hypertension* 60: 269-275, 2012.
Joshi SR, Corner BS, McLendon JM, and Gerthoffer WT. MicroRNA Regulation of Smooth Muscle Phenotype. *Molecular and Cellular Pharmacology* 4: 1-16, 2012.
Leopold JA, Walker J, Scribner AW, Voetsch B, Zhang YY, Loscalzo AJ, Stanton RC, and Loscalzo J. Glucose-6-phosphate dehydrogenase modulates vascular endothelial growth factor-mediated angiogenesis. *J Biol Chem* 278: 32100-32106, 2003.
Wang X, Liu H, Zhang X, Li X, Gu H, Zhang H, and Fan R. G6PD downregulation triggered growth inhibition and induced apoptosis by regulating STAT3 signaling pathway in esophageal squamous cell carcinoma. *Tumour Biol* 37: 781-789, 2016.

\* cited by examiner

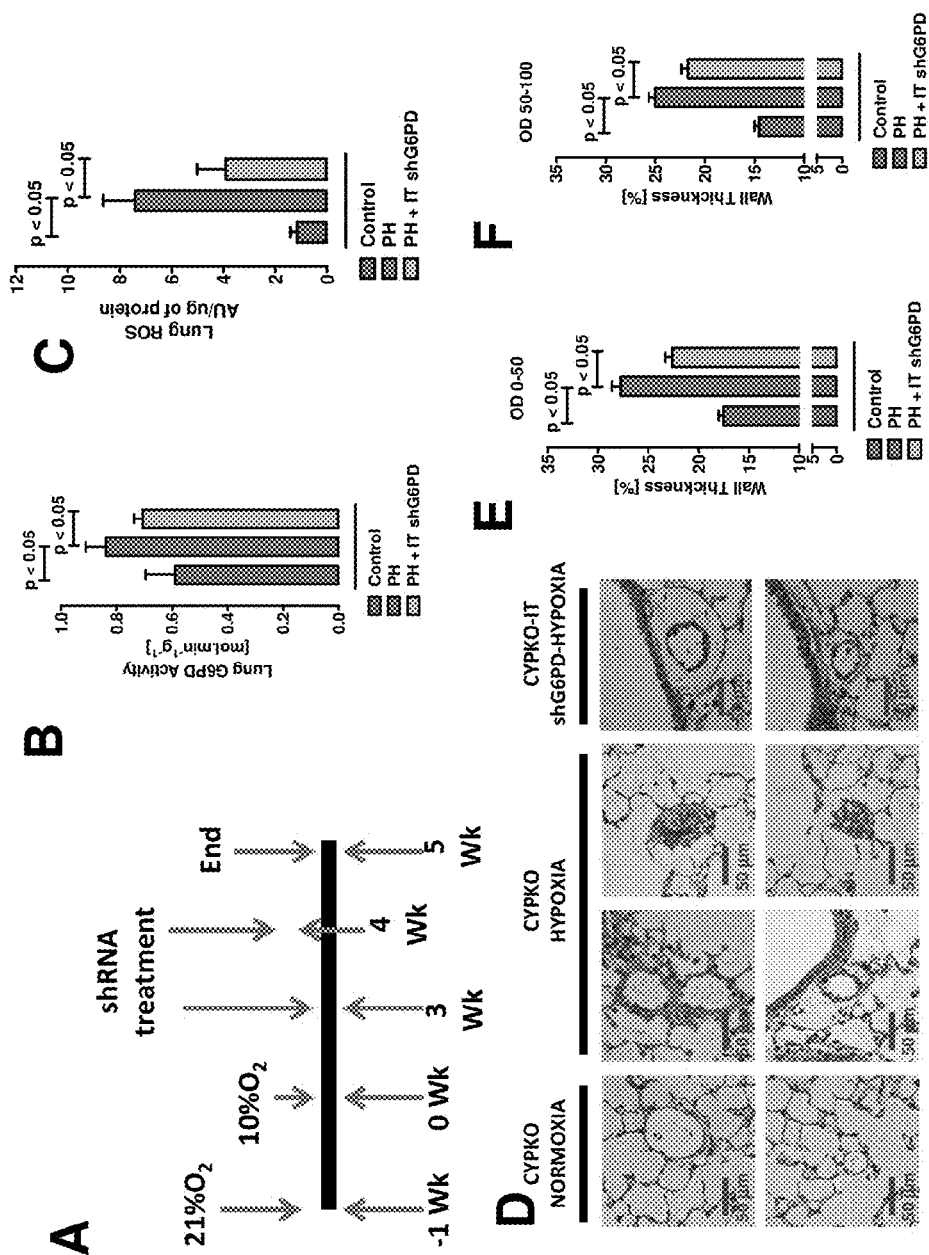
Figures 2A-F

Figures 3A-G
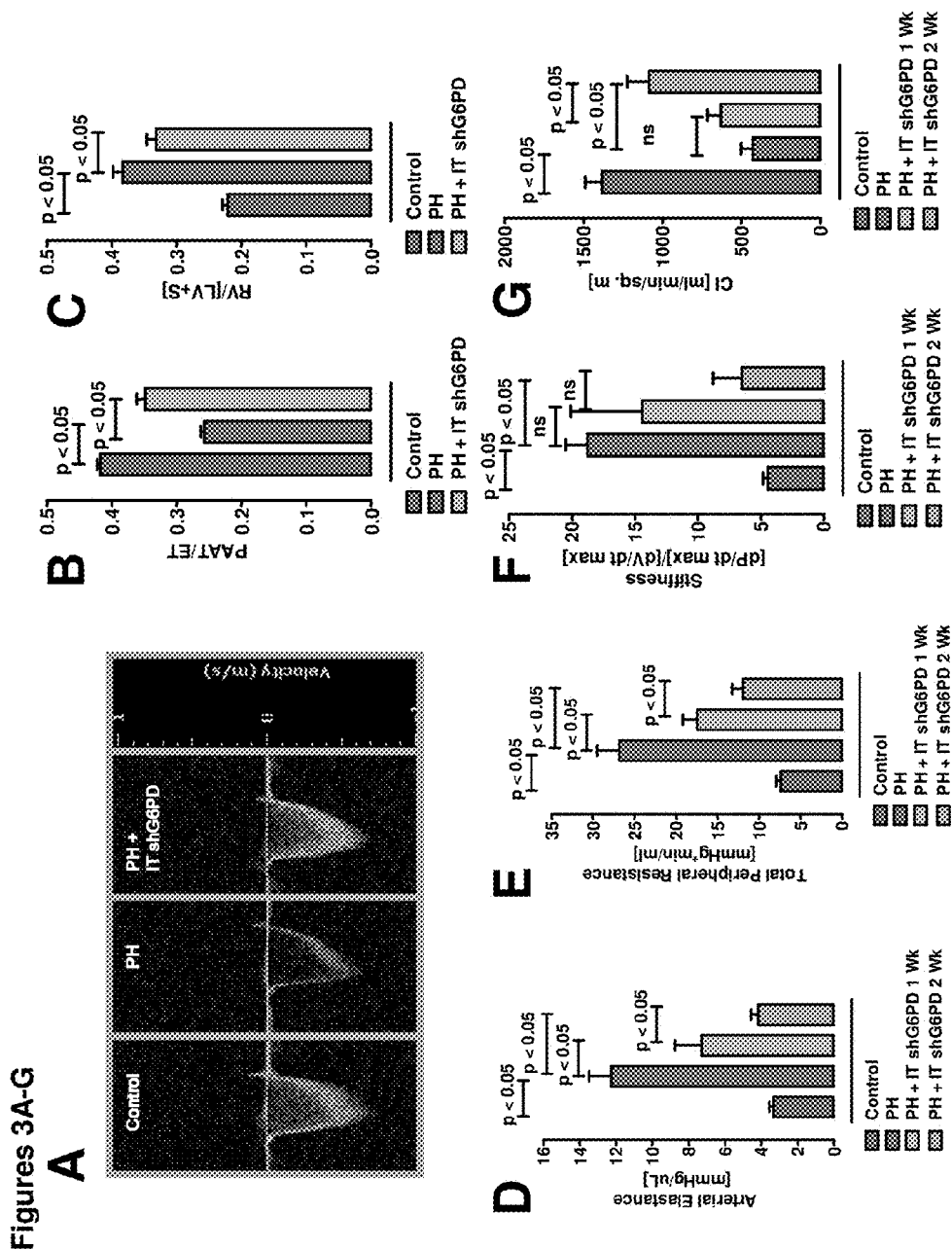

Figures 4A-B
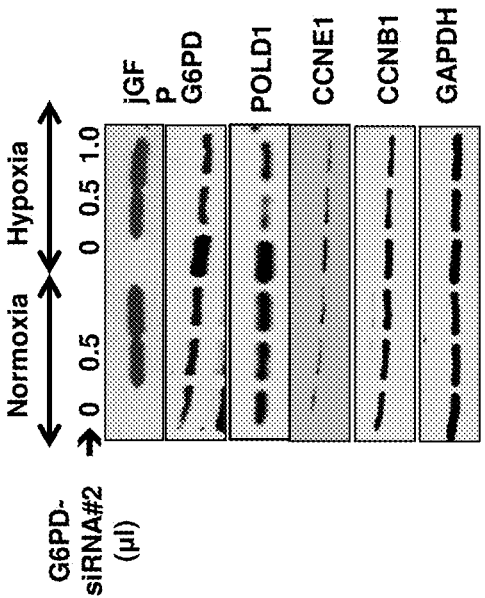
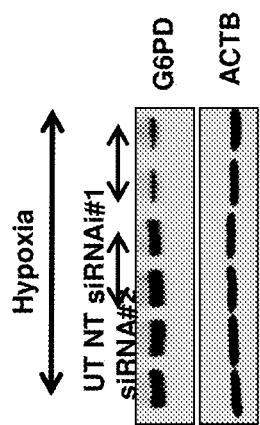

RNAI INHIBITORS OF GLUCOSE-6-PHOSPHATE DEHYDROGENASE FOR TREATING CARDIOVASCULAR AND PULMONARY CONDITIONS

CROSS REFERENCE TO RELATED APPLICATION

This application claims priority to U.S. Provisional Application No. 62/422,985, filed on Nov. 16, 2016, the content of which is incorporated by reference herein in its entirety.

INCORPORATION-BY-REFERENCE OF SEQUENCE LISTING

A sequence listing, filed as the ASCII text file "11018_005449US1_ST25_V3" having a file size of 4.62 kilobytes, is incorporated herein by reference in its entirety.

FIELD OF THE INVENTION

The present invention relates to treating or preventing cardiovascular diseases using RNA interference (RNAi) to inhibit glucose-6-phosphate dehydrogenase (G6PD).

BACKGROUND

Cardiovascular diseases are among the leading causes of mortality and morbidity worldwide with ever-increasing prevalence. Cardiovascular diseases include numerous conditions that affect the heart, heart valves, blood, and blood vessels (arteries, capillaries, and veins) of the body. The causes of cardiovascular disease are diverse but atherosclerosis and/or hypertension are the most common. Risk factors include elevated plasma total or LDL cholesterol, elevated triglycerides, low HDL cholesterol, e.g. hyperlipidemia, hypercholesterolemia, or hypoalphalipoproteinemia, and increased inflammatory markers such as C-reactive protein and fibrinogen.

Major cardiovascular diseases including stroke, atherosclerosis, and hypertension, as well as orphan diseases such as pulmonary hypertension, angiosarcoma, hemangiosarcoma, and hypertrophic cardiomyopathies, are incurable. In addition, medical therapies to treat congestive heart failure and pulmonary hypertension-associated heart failure are inadequate.

Pulmonary hypertension presents an increase of blood pressure in the pulmonary artery, pulmonary vein, or pulmonary capillaries, together known as the lung vasculature, leading to shortness of breath, dizziness, fainting, leg swelling and other symptoms. Pulmonary circulation is a low resistance, low pressure, and high compliant vascular bed. In pulmonary hypertension, the pressure in the pulmonary artery rises above normal levels. Normally, pulmonary artery pressure is maintained around 20-25 mmHg. Pulmonary hypertension is defined when the pressures increase to more than 30 mmHg. Pulmonary hypertension is a major cause of morbidity and mortality in patients with several different clinical conditions. Pulmonary hypertension is a progressive disease and the pathophysiology of pulmonary hypertension is heterogeneous. Severe pulmonary hypertension remains debilitating and deadly. Pulmonary hypertension is divided into five groups with diverse etiologies. In all forms of pulmonary hypertension, pulmonary artery pressure increases mainly because of increased pulmonary constriction/resistance and narrowing or remodeling of pulmonary artery and veins. One cause of pulmonary hypertension is alveolar hypoxia, which results from localized inadequate ventilation of well-perfused alveoli or from a generalized decrease in alveolar ventilation. Pulmonary hypertension is also a vascular permeability related disease. Current therapies are inadequate to reverse the complex pulmonary vascular remodeling and reduce pulmonary vascular resistance. Pulmonary hypertension has been historically chronic and incurable with a poor survival rate. Treatment of pulmonary hypertension usually involves continuous use of oxygen. Pulmonary vasodilators (e.g., hydralazine, calcium blockers, nitric oxide, protein kinase G activators, prostacyclin, endothelin receptor blockers) have not proven effective, and lung transplant is often required for patients who do not respond to therapy.

Arteriosclerosis, which is induced and progressed by various risk factors, causes thickening of the arterial lumen to interrupt blood flow, resulting in a cardiovascular disease such as aortic aneurysm, angina, myocardial infarction, or cerebral infarction.

Cardiac hypertrophy is an adaptive response of the heart cells to elevated levels of biomechanical stress imposed by a variety of extrinsic and intrinsic stimuli including pressure or volume overload, familial/genetic cardiomyopathies, or loss of contractile mass from preceding infarction (Frey et al. (2004) Circulation 109:1580-1589; Frey et al. (2003) Annu. Rev. Physiol. 65:45-79; Yoshida et al. (1986) J. Cardiogr. 16:399-406). If sustained, hypertrophy often becomes pathological, accompanied by significant risk of arrhythmia, progression to heart failure, and sudden death (Frey et al. (2004), supra; Levy et al. (1990) N. Engl. J. Med. 322:1561-1566; Koren et al. (1991) Ann. Intern. Med. 114:345-352). At the molecular level, pathological hypertrophy is associated with re-induction of the so-called fetal gene program in which the fetal isoforms of genes responsible for regulating cardiac contractility and calcium handling (e.g. .beta.-MHC) are upregulated (Frey et al. (2004), supra; Frey et al. (2003), supra); Olson (2004) Nat. Med. 10:467-474; Iemitsu et al. (2001) Am. J. Physiol. Regul. Integr. Comp. Physiol. 281:R2029-2036). At the cellular level, the main characteristics of ventricular hypertrophic growth are enhanced protein synthesis and an increase in size of cardiomyocytes (Frey et al. (2004), supra; Frey et al. (2003), supra). As pathologic hypertrophy progresses, these changes in molecular and cellular phenotypes are accompanied by an increase in apoptosis, fibrosis, chamber dilation, and decreased systolic function (Frey et al. (2004), supra).

Heart failure is associated with high morbidity as well as significant mortality. The clinical syndrome of heart failure is the result of heterogeneous myocardial or vascular diseases, and is defined by insufficiency to maintain blood circulation throughout the body. Despite significant advances in the clinical management of heart failure, conventional therapies are ultimately ineffective in many patients who progress to advanced heart failure. In these cases, implantation of left ventricular assist devices (LVAD) and/or heart transplantation can be the only viable options.

In view of the foregoing, there is a need to develop effective treatments for various cardiovascular disorders. In this disclosure, novel therapies to treat cardiovascular disorders, such as pulmonary hypertension, pulmonary hypertension-associated heart failure, and cardiomyopathies, are described.

SUMMARY OF THE INVENTION

In certain embodiments, the present invention relates to a method for treating or preventing a cardiovascular disorder and/or a pulmonary disorder in a subject in need thereof, comprising administering to the subject a therapeutically effective amount of a polynucleotide inhibitor of Glucose-6-phosphate dehydrogenase (G6PD) or a nucleic acid encoding G6PD.

In additional embodiments, the polynucleotide inhibitor comprises an RNA interference (RNAi) inhibitor. In additional embodiments, the polynucleotide inhibitor comprises a small interfering RNA (siRNA), a short hairpin RNA (shRNA), or a combination thereof. In additional embodiments, the polynucleotide inhibitor comprises an antisense oligonucleotide targeting a nucleic acid encoding the human G6PD (e.g., human G6PD 545 encoded by the sequence set forth in SEQ ID NO. 1).

In further embodiments, the polynucleotide inhibitor comprises the nucleotide sequence set forth in SEQ ID NO:2, SEQ ID NO:4, SEQ ID NO:5, SEQ ID NO:6, SEQ ID NO:7, SEQ ID NO:9, SEQ ID NO:10, SEQ ID NO:11, SEQ ID NO:12, or combinations thereof.

In additional embodiments, the cardiovascular disorder comprises pulmonary hypertension, pulmonary hypertension-associated heart failure, cardiomyopathies, hypertension, stroke, ischemic cardiomyopathy, medial hypertrophy, acute neointimal formation following iatrogenic interventions, atherosclerosis, congestive heart failure, or combinations thereof.

In additional embodiments, the cardiovascular disorder and/or a pulmonary disorder comprises angiosarcoma, hemangioscarcoma, Timothy Syndrome, hypertrophic cardiomyopathy, or combinations thereof. In further embodiments, the cardiovascular disorder and/or pulmonary disorder comprises any of the groups of pulmonary hypertension 1-5, or combinations thereof. In additional embodiments, the disorder comprises scleroderma, categorized as pulmonary hypertension group I.

In additional embodiments, the method further comprises treating the subject with a diuretic, a vasodilator, an inotropic agent, an angiotensin converting enzyme (ACE) inhibitor, a beta blocker, a neurohumoral blocker, an aldosterone antagonist, erythropoietin, or combinations thereof.

In additional embodiments, the method further comprises treating the subject with a medical device and/or surgery.

In additional embodiments, the medical device is a bi-ventricular pacemaker, an implantable cardioverter-defibrillator (ICD), a ventricular assist device (VAD), a left ventricular assist device (LVAD), a cardiac resynchronization therapy (CRT), or combinations thereof.

In additional embodiments, the composition comprises a polynucleotide inhibitor of Glucose-6-phosphate dehydrogenase (G6PD) or a nucleic acid encoding G6PD.

In additional embodiments, the invention relates to a pharmaceutical composition of any of the inhibitors described herein.

In further embodiments, the invention relates to the preparation of a pharmaceutical composition for treating or preventing a cardiovascular disorder and/or a pulmonary disorder in a subject in need thereof.

In certain embodiment, the present disclosure provides for a method of treating or preventing a cardiovascular disorder and/or a pulmonary disorder in a subject in need thereof, comprising administering the present composition to the subject.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

FIGS. 2A-2F are graphs and images shows that pulmonary hypertension (PH) was induced by exposing mice to 10% 02. Control and PH mice were treated with CYPKO-IT-GFP (CYPKO) and CYPKO-IT-shG6PD-GFP, respectively. (FIG. 2A) Graphic representation of the treatment regime. Mice were treated by intra-tracheal spray (25 µl of 100 ng-CYPKO and CYPKO-IT-shG6PD-GFP, respectively) once per week for two weeks. (FIG. 2B) Estimation of G6PD activity in Control, PH and PH+ shG6PD treated mice. (FIG. 2C) Estimation of reactive oxygen species (ROS) in Control, PH and PH+ shG6PD treated mice. (FIG. 2D) H&E staining to demonstrate pulmonary artery remodeling and occlusive lesion in CYPKO and CYPKO-IT-shG6PD-GFP treated mice. (FIGS. 2E-2F) graphic representation of the number of remodeled pulmonary arteries with medial wall thickening in CYPKO CYPKO-IT-shG6PD-GFP treated mice.

FIGS. 3A-3G are graphs and images showing that pulmonary hypertension (PH) was induced by exposing mice to 10% 02. Control and PH mice were treated with CYPKO-IT-GFP (CYPKO) and CYPKO-IT-shG6PD-GFP, respectively, for 2 weeks. Pulmonary resistance was determined by PAAT-to-ET (FIGS. 3A-B), right ventricle (RV) hypertrophy was determined by RV-to-left ventricle+septum ratio (FIG. 3C). Arterial elastance (FIG. 3D), total peripheral resistance (FIG. 3E), LV stiffness (FIG. 3F), and cardiac index (CI) (FIG. 3G) was determined in Control, PH and PH+ shG6PD treated mice.

FIGS. 4A-4B are blots showing rat pulmonary artery smooth muscle cells that were cultured in 15% DMEM for 48 hr and transfected with G6PD-siRNA#1 and G6PD-siRNA#2, respectively (0.5 and 1.0 µl=50 ng and 100 ng, respectively). The cells were then subjected to hypoxia (1% 02) for 72 hr. Expression of G6PD protein was estimated using western blot analyses. UT=Untransfected; NT=non-targeting/scrambled sequence (FIG. 4A). Beta-Actin (ACTB) was used as loading control. FIG. 4B are blots showing the effect of G6PD-siRNA#2 treatment, on the expression of G6PD (FIG. 4B-panel 2), polymerase delta (FIG. 4B-panel 3), cyclin E1 (FIG. 4B-panel 4), and cyclin B (FIG. 4B-panel 5), under normoxic and hypoxic conditions, in these cells were determined using Western blot analyses. GAPDH was used as a loading control.

DETAILED DESCRIPTION

Figure 1:
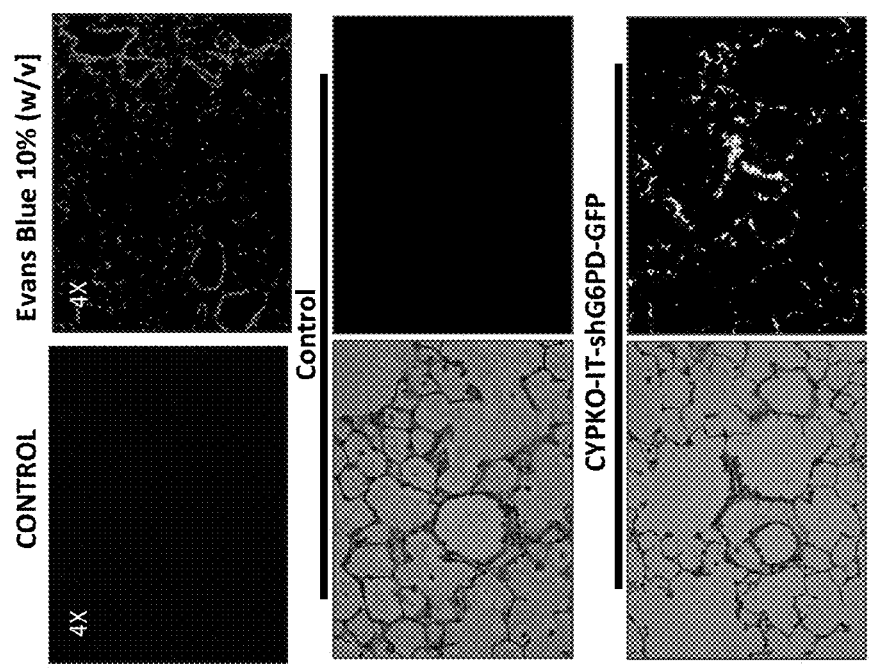
FIG. 1 contains images showing that pulmonary hypertension (PH) was induced by exposing mice to 10% 02. Control and PH mice were treated with CYPKO-IT-GFP (Control) and CYPKO-IT-shG6PD-GFP, respectively. Images and graphics demonstrate the distribution of Evan blue and expression of GFP-tagged G6PD-shRNA in mice lungs.

As described herein we provide methods as well as one or more agents/compounds that silence or inhibit G6PD for the treatment, prophylaxis or alleviation of cardiovascular conditions described herein, or related pulmonary conditions, or predisposition to such a condition.

The present disclosure provides for methods of treating or preventing a cardiovascular disorder and/or a related pulmonary disorder in a subject. In the method, a therapeutically effective amount of a polynucleotide inhibitor of Glucose-6-phosphate dehydrogenase (G6PD) or a nucleic acid encoding G6PD is administered. The polynucleotide inhibitor may be an RNA interference (RNAi) inhibitor, such as a small interfering RNA (siRNA), a short hairpin RNA (shRNA), microRNA (miR) or a combination thereof. The polynucleotide inhibitor may also be an antisense oligonucleotide targeting a nucleic acid encoding G6PD (e.g., mRNA etc.)

In certain embodiments, the present agent/composition is specifically administered to lung or cardiac cells, to inhibit gene function and prevent one or more of the symptoms and processes associated with the progression of cardiovascular or pulmonary conditions. Such treatment may also be useful in treating patients who already exhibit cardiovascular or pulmonary conditions, to reverse or alleviate one or more of the disease processes. Additionally, approaches utilizing one or more additional inhibitors including an inhibitor of protein kinase G and blocker of endothelin A or B receptor or any combination of these, are also expected to be useful for treating certain conditions.

Glucose-6-Phosphate Dehydrogenase (G6PD)

Glucose-6-phosphate dehydrogenase (G6PD) generates nicotinamide adenine dinucleotide phosphate reduced (NADPH), a key cofactor for various redox-sensitive enzymes like: NADPH oxidases, glutathione/thioredoxin reductases, and other reductive and anabolic reactions in the cell (14). We have shown that G6PD is involved in regulation of coronary and pulmonary artery contraction and relaxation (3), and pulmonary artery SMC phenotype (12). Glucose-6-phosphate dehydrogenase has been shown to be associated with progressive pulmonary artery remodeling in pulmonary hypertension.

Glycolysis, glucose flux through the PPP, and the activity of NADPH producing isocitrate dehydrogenase-1 and -2 are increased in pulmonary artery of idiopathic- and heritable-pulmonary hypertension patients, and in endothelial cells and fibroblasts from idiopathic pulmonary hypertension patients. G6PD expression and activity are increased in: (a) endothelin-1 treated pulmonary artery smooth muscle cells from pulmonary hypertension patients; (b) hypoxic cultured rat pulmonary artery smooth muscle cells; and (c) lungs of pulmonary hypertensive rat models. G6PD is a major supplier of NADPH (60% by G6PD+40% by isocitrate dehydrogenase) for: anabolic reactions and superoxide production from NADPH oxidases in the cell. Excess NADPH generation contributes to pathogenic "reductive stress" in cardiovascular system.

G6PD-derived NADPH plays a key role in stimulating proliferation and inhibiting apoptosis of cells (5). Ectopic expression of G6PD increases rat PASMC proliferation (10) and contributes to the HIF1α-induced endothelial growth (16). Additionally, our findings suggest that hyper-activation of G6PD in CD133$^+$ progenitor cells promote their self-renewal (11). CD133$^+$ cells potentially participate in the PA remodeling process in PAH (2). Conversely, inhibition of G6PD increases the rate of apoptosis of X laevis oocytes, HEK293 cells, esophageal squamous cell carcinoma, and melanoma cells (4, 7, 17, 19). In PH, the PASMC and endothelial cell proliferation is accompanied by decreased expression of pro-apoptotic genes (6). Therefore, altogether these findings allude stimulation of G6PD activity by endothelin-1 or by hypoxia likely inhibits apoptosis and promotes proliferation of PASMC, and contributes to progressive PA remodeling and to the pathogenesis of HPH and PAH.

G6PD deficiency is common in humans, and 400-point mutations have been found in this enzyme in different ethnic groups around the world. Epidemiological studies suggest that individuals who harbor a Mediterranean-type non-synonymous mutation [single nucleotide polymorphism in exon 6: dbSNP rs5030868] have 80% less G6PD activity as compared to normal individuals and are less likely to have cardiovascular diseases (13), including sickle cell anemia-associated PH.

Other methods of modulating G6PD gene expression are known to those skilled in the art and include dominant negative approaches. An example of this approach, which could be utilized in the context of inhibiting, preventing, or treating a cardiovascular disorder or related pulmonary conditions is utilizing a G6PD mutant or a small molecule chemical or mimetic which can reduce or inhibit the level and/or activity of G6PD. Yet another approach is to use non-functional variants of G6PD polypeptide that compete with the endogenous gene product resulting in inhibition of function. Inhibitors of G6PD interacting proteins can be targeted, and these are also expected to serve as useful in the context of inhibiting, preventing, or treating a cardiovascular disorder or related pulmonary related conditions.

G6PD gene expression may also be modulated by introducing peptides or small molecules which inhibit gene expression or functional activity. Thus, compounds identified by the assays described herein as binding to or modulating, such as down-regulating, the amount, activity or expression of G6PD polypeptide may be administered to a subject to prevent or diminish the function of G6PD polypeptide. Such a compound may be administered along with a pharmaceutically acceptable carrier in an amount effective to down-regulate expression or activity G6PD, or by activating or down-regulating a second signal which controls G6PD expression, activity or amount, and thereby alleviating the abnormal condition.

Alternatively, gene therapy may be employed to control the endogenous production of G6PD by the relevant cells in the subject. For example, a polynucleotide encoding a G6PD siRNA or a portion of this may be engineered for expression in a replication defective retroviral vector. The retroviral expression construct may then be isolated and introduced into a packaging cell transduced with a retroviral plasmid vector containing RNA encoding an anti-G6PD siRNA such that the packaging cell now produces infectious viral particles containing the sequence of interest. These producer cells may be administered to a subject for engineering cells in vivo and regulating expression of the G6PD polypeptide in vivo. For overview of gene therapy, see Chapter 20, Gene Therapy and other Molecular Genetic-based Therapeutic Approaches, (and references cited therein) in Human Molecular Genetics, T Strachan and A P Read, BIOS Scientific Publishers Ltd (1996).

In some embodiments, the level of G6PD is decreased in a cardiac and/or lung cells. In certain embodiments, treatment may be targeted to, or specific to, diseased cells. The expression of G6PD may be specifically decreased only in diseased cells (i.e., those cells which are predisposed to the cardiovascular condition and/or related pulmonary condition, or exhibiting cardiovascular condition and/or related pulmonary condition already), and not substantially in other non-diseased cells. In these methods, expression of G6PD may not be substantially reduced in other cells, i.e., cells which are non-diseased cells. Thus, in such embodiments, the level of G6PD remains substantially the same or similar in non-diseased cells in the course of or following treatment.

Cell specific reduction of G6PD levels and/or activity may be achieved by targeted administration, i.e., applying the treatment only to the targeted cells and not other cells. However, in other embodiments, down-regulation of G6PD expression in other cells (e.g., a portion of non-diseased cells, and not substantially in other cell or tissue types) is employed.

In certain embodiments, cardiac and/or lung cell specific expression vectors are used for specific expression of for example siRNAs.

The methods and compositions described here may reduce the level and/or activity of G6PD, G6PD polynucleotides, G6PD nucleotides and G6PD nucleic acids, as well as variants, homologues, derivatives and fragments of any of these. The inhibitors targeting G6PD may also be used for the methods of treatment or prophylaxis described.

The terms "G6PD polynucleotide", "G6PD nucleotide" and "G6PD nucleic acid," "G6PD nucleic acid" may be used interchangeably, and should be understood to specifically include both cDNA and genomic G6PD sequences. These terms are also intended to include a nucleic acid sequence capable of encoding a G6PD polypeptide and/or a fragment, derivative, homologue or variant of this.

By "down-regulation" or "reduction" is meant any negative effect on the condition being studied; this may be total or partial. Thus, where the level or activity of a protein is being detected, the present agent is capable of reducing, ameliorating, or abolishing the level or activity of the protein. The down-regulation of the level or activity of the protein achieved by the present agent may be at least 10%, such as at least 20%, at least 30%, at least 40%, at least 50%, at least 60%, at least 70%, at least 80%, at least 90% or more compared to the level or activity of the protein in the absence of the present agent.

The term "compound" refers to a chemical compound (naturally occurring or synthesized), such as a biological macromolecule (e.g., nucleic acid, protein, non-peptide, or organic molecule), or an extract made from biological materials such as bacteria, plants, fungi, or animal (particularly mammalian) cells or tissues, or even an inorganic element or molecule. The compound may be an antibody.

Non-limiting examples of potential inhibitors or antagonists of G6PD include nucleotides and their analogues, including purines and purine analogues, oligonucleotides or proteins which are closely related to a binding partner of G6PD, e.g., a fragment of the binding partner, or small molecules which bind to the G6PD polypeptide but do not elicit a response, so that the activity of the polypeptide is prevented, etc.

In some embodiments, the anti-G6PD agent is provided as an injectable or intravenous composition and administered accordingly. The dosage of the anti-G6PD agent inhibitor may be between about 5 mg/kg/2 weeks to about 10 mg/kg/2 weeks. The anti-G6PD agent inhibitor may be provided in a dosage of between 10-300 mg/day, such as at least 30 mg/day, less than 200 mg/day or between 30 mg/day to 200 mg/day.

The anti-G6PD agent may downregulate G6PD by RNA interference, such as by comprising a Small Interfering RNA (siRNA) or Short Hairpin RNA (shRNA) or Micro RNA (miRNA). In certain embodiments, such agents are synthetic or recombinant nucleotides.

Additionally, G6PD polypeptide fragments could be utilized as inhibitors.

Polynucleotides targeting G6PD may comprise nucleotide sequences that are at least about 70% identical, preferably at least about 80% identical, more preferably at least about 90% identical and most preferably at least about 95% identical (e.g., 95%, 96%, 97%, 98%, 99%, 100%) to a target sequence which is a part of a polynucleotide encoding human G6PD545 or human G6PD515 gene sequences with reference to sequences described above, when the comparison is performed by a BLAST nucleotide algorithm wherein the parameters of the algorithm are selected to give the largest match between the respective sequences over the entire length of the respective reference sequences.

Sequence identity refers to the degree to which the nucleotides of two polynucleotides are the same at equivalent positions when the two sequences are optimally aligned. Sequence similarity includes identical nucleotides and non-identical, biochemically related nucleotides.

"Homology" refers to sequence similarity between two polynucleotide sequences or between two polypeptide sequences when they are optimally aligned. When a position in both of the two compared sequences is occupied by the same base or amino acid monomer subunit, e.g., if a position in each of two DNA molecules is occupied by adenine, then the molecules are homologous at that position. The percent of homology is the number of homologous positions shared by the two sequences divided by the total number of positions compared ×100. For example, if 6 of 10 of the positions in two sequences are matched or homologous when the sequences are optimally aligned then the two sequences are 60% homologous. Generally, the comparison is made when two sequences are aligned to give maximum percent homology.

The following references relate to BLAST algorithms often used for sequence analysis: BLAST ALGORITHMS: Altschul, S. F., et al., (1990) J. Mol. Biol. 215:403-410; Gish, W., et al., (1993) Nature Genet. 3:266-272; Madden, T. L., et al., (1996) Meth. Enzymol. 266:131-141; Altschul, S. F., et al., (1997) Nucleic Acids Res. 25:3389-3402; Zhang, J., et al., (1997) Genome Res. 7:649-656; Wootton, J. C., et al., (1993) Comput. Chem. 17:149-163; Hancock, J. M. et al., (1994) Comput. Appl. Biosci. 10:67-70; ALIGNMENT SCORING SYSTEMS: Dayhoff, M. O., et al., "A model of evolutionary change in proteins." in Atlas of Protein Sequence and Structure, (1978) vol. 5, suppl. 3. M. O. Dayhoff (ed.), pp. 345-352, Natl. Biomed. Res. Found., Washington, D.C.; Schwartz, R. M., et al., "Matrices for detecting distant relationships." in Atlas of Protein Sequence and Structure, (1978) vol. 5, suppl. 3." M. O. Dayhoff (ed.), pp. 353-358, Natl. Biomed. Res. Found., Washington, D.C.; Altschul, S. F., (1991) J. Mol. Biol. 219:555-565; States, D. J., et al., (1991) Methods 3:66-70; Henikoff, S., et al., (1992) Proc. Natl. Acad. Sci. USA 89:10915-10919; Altschul, S. F., et al., (1993) J. Mol. Evol. 36:290-300; ALIGNMENT STATISTICS: Karlin, S., et al., (1990) Proc. Natl. Acad. Sci. USA 87:2264-2268; Karlin, S., et al., (1993) Proc. Natl. Acad. Sci. USA 90:5873-5877; Dembo, A., et al., (1994) Ann. Prob. 22:2022-2039; and Altschul, S. F. "Evaluating the statistical significance of multiple distinct local alignments." in Theoretical and Computational Methods in Genome Research (S. Suhai, ed.), (1997) pp. 1-14, Plenum, N.Y.

In certain aspects, the present invention also provides expression vectors comprising various nucleic acids, wherein the nucleic acid is operably linked to control sequences that are recognized by a host cell when the host cell is transfected with the vector.

Inhibitory Nucleic Acids

Any number of means for inhibiting G6PD activity or gene expression can be used in the methods of the invention. It is noted that in addition to G6PD, G6PD isoforms or 6-phosphogluconorate dehydrogenase is another process which could potentially be blocked by inhibitory compounds in a similar manner as described herein for G6PD.

For example, a nucleic acid molecule complementary to at least a portion of a human G6PD encoding nucleic acid can be used to inhibit G6PD gene expression. Means for inhibiting gene expression using short RNA molecules, for example, are known. Among these are short interfering RNA (siRNA), small temporal RNAs (stRNAs), and micro-RNAs (miRNAs). Short interfering RNAs silence genes through an mRNA degradation pathway, while stRNAs and miRNAs are short RNAs that are processed from endogenously encoded hairpin-structured precursors, and function to silence genes via translational repression. See, e.g., McManus et al., RNA, 8(6):842-50 (2002); Morris et al., Science, 305(5688):1289-92 (2004); He and Hannon, Nat Rev Genet. 5(7):522-31 (2004).

RNA Interference

"RNA interference, or RNAi" a form of post-transcriptional gene silencing ("PTGS"), describes effects that result from the introduction of double-stranded RNA into cells (reviewed in Fire, A. Trends Genet 15:358-363 (1999); Sharp, P. Genes Dev 13:139-141 (1999); Hunter, C. Curr Biol 9:R440-R442 (1999); Baulcombe. D. Curr Biol 9:R599-R601 (1999); Vaucheret et al. Plant J 16: 651-659 (1998)). RNA interference, commonly referred to as RNAi, offers a way of specifically inactivating a cloned gene, and is a powerful tool for investigating gene function.

The active agent in RNAi is a long double-stranded (antiparallel duplex) RNA, with one of the strands corresponding or complementary to the RNA which is to be inhibited. The inhibited RNA is the target RNA. The long double-stranded RNA is chopped into smaller duplexes of approximately 20 to 25 nucleotide pairs, after which the mechanism by which the smaller RNAs inhibit expression of the target is largely unknown at this time. While RNAi was shown initially to work well in lower eukaryotes, for mammalian cells, it was thought that RNAi might be suitable only for studies on the oocyte and the preimplantation embryo.

More recently, it was shown that RNAi would work in human cells if the RNA strands were provided as pre-sized duplexes of about 19 nucleotide pairs, and RNAi worked particularly well with small unpaired 3' extensions on the end of each strand (Elbashir et al. Nature 411: 494-498 (2001)). In this report, "short interfering RNA" (siRNA, also referred to as small interfering RNA) were applied to cultured cells by transfection in oligofectamine micelles. These RNA duplexes were too short to elicit sequence-nonspecific responses like apoptosis, yet they efficiently initiated RNAi. Many laboratories then tested the use of siRNA to knock out target genes in mammalian cells. The results demonstrated that siRNA works quite well in most instances.

For purposes of reducing the activity of G6PD, RNAi molecules (e.g., siRNAs, shRNAs, etc.) targeting the gene encoding the G6PD or a G6PD mRNA can be specifically designed using computer programs. Illustrative nucleotide sequences encoding the amino acid sequences of human G6PD variant 1 and 2 are known and published, e.g., in GenBank Accession No. NM_000402.3 (older version) or NM 000402.4 (for variant 1) etc.

Software programs for predicting siRNA sequences to inhibit the expression of a target protein are commercially available and find use. One program, siDESIGN from Dharmacon, Inc. (Lafayette, Colo.), permits predicting siRNAs for any nucleic acid sequence, and is available on the internet at dharmacon.com. Programs for designing siRNAs are also available from others, including Genscript (available on the internet at genscript.com/ssl-bin/app/rnai) and, to academic and non-profit researchers, from the Whitehead Institute for Biomedical Research found on the worldwide web at "jura.wi.mit.edu/pubint/http://iona.wi.mit.edu/siRNAext/."

Any suitable viral knockdown system could be utilized for decreasing G6PD mRNA levels—including AAV, adenoviral and/or lentiviral vectors, or other suitable vectors that are capable of being targeted specifically to the liver. (See Zuckerman and Davis 2015).

Additionally, specifically targeted delivery of shG6PD mRNA or other G6PD blocking molecule (nucleic acid, peptide, or small molecule) could be delivered by targeted liposome, nanoparticle or other suitable means.

In a particular example, cardiovascular or pulmonary conditions may be treated or prevented by reducing the amount, expression or activity of G6PD in whole or in part, for example by siRNAs capable of binding to and destroying G6PD mRNA. Examples of such anti-G6PD agents/compounds are provided herein, which function to downregulate G6PD by mRNA interference. The anti-G6PD agent/compound may comprise a Small Interfering RNA (siRNA) or Short Hairpin RNA (shRNA). Specific examples of an anti-G6PD agent includes any of SEQ ID NO:2, SEQ ID NO:4, SEQ ID NO:5, SEQ ID NO:6, SEQ ID NO:7, SEQ ID NO:9, SEQ ID NO:10, SEQ ID NO:11, SEQ ID NO:12 or combinations thereof, which may be useful in certain embodiments as described below and in the Examples.

RNA interference (RNAi) is a method of post transcriptional gene silencing (PTGS) induced by the direct introduction of double-stranded RNA (dsRNA) and has emerged as a useful tool to knock out expression of specific genes in a variety of organisms. RNAi is described by Fire et al., Nature 391:806-811 (1998). Other methods of PTGS are known and include, for example, introduction of a transgene or virus. Generally, in PTGS, the transcript of the silenced gene is synthesized but does not accumulate because it is rapidly degraded. Methods for PTGS, including RNAi are described, for example, in the Ambion.com world wide web site, in the directory "/hottopics/", in the "rnai" file.

Suitable methods for RNAi in vitro are described herein. One such method involves the introduction of siRNA (small interfering RNA). Current models indicate that these 21-23 nucleotide dsRNAs can induce PTGS. Methods for designing effective siRNAs are described, for example, in the Ambion web site described above. RNA precursors such as Short Hairpin RNAs (shRNAs) can also be encoded by all or a part of the G6PD nucleic acid sequence.

Alternatively, double-stranded (ds) RNA is a powerful way of interfering with gene expression in a range of organisms that has recently been shown to be successful in mammals (Wianny and Zernicka-Goetz, 2000, Nat Cell Biol 2:70-75). Double stranded RNA corresponding to the sequence of a G6PD polynucleotide can be introduced into or expressed in oocytes and cells of a candidate organism to interfere with G6PD activity.

In certain embodiments, RNAi is caused by decreasing the activity of an mRNA, such as by causing the destruction of specific mRNA molecules, and/or by preventing an mRNA from producing a protein.

In certain embodiments, siRNAs (small interfering RNAs) or small-hairpin RNA (shRNA) are used to reduce the level and/or activity of G6PD. In certain embodiments, microRNAs (miRNAs) are used to reduce the level and/or activity of G6PD.

SiRNAs may have 16-30 nucleotides, e.g., 16, 17, 18, 19, 20, 21, 22, 23, 24, 25, 26, 27, 28, 29, or 30 nucleotides. The siRNAs may have fewer than 16 or more than 30 nucleotides. The polynucleotides of the invention include both unmodified siRNAs and modified siRNAs such as siRNA derivatives etc.

SiRNAs can be delivered into cells in vitro or in vivo by methods known in the art, including cationic liposome transfection and electroporation. SiRNAs and shRNA molecules can be delivered to cells using viruses or DNA vectors.

Antisense Oligonucleotide

In certain embodiments, an approach for therapy of such disorders is to express anti-sense constructs directed against G6PD polynucleotides as described herein.

Anti-sense constructs may be used to inhibit gene function to prevent or treat cardiovascular or pulmonary conditions. Antisense constructs, i.e., nucleic acid, such as RNA, constructs complementary to the sense nucleic acid or mRNA, are described in detail in U.S. Pat. No. 6,100,090 (Monia et al.), and Neckers et al., 1992, Crit Rev Oncog 3(1-2):175-231.

In certain embodiments, an antisense oligonucleotide is used to reduce or inhibit the level and/or activity of G6PD.

Antisense oligonucleotides may be ribonucleotides or deoxyribonucleotides. In certain embodiments, the antisense oligonucleotide therapeutics may have at least one chemical modification (i.e., the oligonucleotide is chemically modified). For instance, suitable antisense oligonucleotides may be comprised of one or more conformationally constrained or bicyclic sugar nucleoside modifications, for example, locked nucleic acids (LNAs).

Alternatively, the antisense oligonucleotides may comprise peptide nucleic acids (PNAs), which contain a peptide-based backbone rather than a sugar-phosphate backbone. Other chemical modifications that the antisense oligonucleotides may contain include, but are not limited to, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages (U.S. Pat. Nos. 6,693,187 and 7,067,641). For instance, antisense oligonucleotides, particularly those of shorter lengths (e.g., less than 15 nucleotides) can comprise one or more affinity enhancing modifications, such as, but not limited to, LNAs, bicyclic nucleosides, phosphonoformates, 2' O alkyl and the like.

In certain embodiments, suitable antisense oligonucleotides are 2'-O-methoxyethyl gapmers which contain 2'-O-methoxyethyl-modified ribonucleotides on both 5' and 3' ends with at least ten deoxyribonucleotides in the center. These gapmers are capable of triggering RNase H-dependent degradation mechanisms of RNA targets. Other modifications of antisense oligonucleotides to enhance stability and improve efficacy, such as those described in U.S. Pat. No. 6,838,283, which is herein incorporated by reference in its entirety, are known in the art and are suitable for use in the present methods. In certain embodiments, antisense oligonucleotides useful for reducing or inhibiting the activity and/or level of G6PD are about 5 to about 50 nucleotides in length, about 10 to about 30 nucleotides in length, about 8 to about 18 nucleotides, about 12 to 16 nucleotides, about 8 nucleotides or greater, or about 20 to about 25 nucleotides in length.

In certain embodiments, antisense oligonucleotides may comprise a sequence that is at least partially complementary to a G6PD mRNA sequence, e.g., at least about 75%, 80%, 85%, 90%, 95%, 96%, 97%, 98%, or 99% complementary to a G6PD mRNA sequence. In some embodiments, the antisense oligonucleotide may be substantially complementary to a G6PD mRNA sequence, that is at least about 95%, 96%, 97%, 98%, or 99% complementary to a target G6PD mRNA sequence. In one embodiment, the antisense oligonucleotide comprises a sequence that is 100% complementary to a G6PD mRNA sequence.

Locked nucleic acids (LNAs) are modified nucleotides that contain an extra bridge between the 2' and 4' carbons of the ribose sugar moiety resulting in a locked conformation that confers enhanced thermal stability to oligonucleotides containing the LNAs. LNAs are described, for example, in U.S. Pat. No. 6,268,490, U.S. Pat. No. 6,316,198, U.S. Pat. No. 6,403,566, U.S. Pat. No. 6,770,748, U.S. Pat. No. 6,833,361, U.S. Pat. No. 6,998,484, U.S. Pat. No. 6,670,461, and U.S. Pat. No. 7,034,133.

In other embodiments, the antisense oligonucleotides are antagomirs. Antagomirs are single-stranded, chemically-modified ribonucleotides that are at least partially complementary to the G6PD mRNA sequence. Antagomirs may comprise one or more modified nucleotides, such as 2'-O-methyl-sugar modifications. In some embodiments, antagomirs comprise only modified nucleotides. Antagomirs may also comprise one or more phosphorothioate linkages resulting in a partial or full phosphorothioate backbone. To facilitate in vivo delivery and stability, the antagomir may be linked to a steroid such as cholesterol, a fatty acid, a vitamin, a carbohydrate, a peptide or another small molecule ligand at its 3' end. Antagomirs suitable for inhibiting or reducing the level and/or activity of G6PD may be about 15 to about 50 nucleotides in length, about 18 to about 30 nucleotides in length, or about 20 to about 25 nucleotides in length. "Partially complementary" refers to a sequence that is at least about 75%, 80%, 85%, 90%, 95%, 96%, 97%, 98%, or 99% complementary to a target polynucleotide sequence. The antagomirs may be at least about 75%, 80%, 85%, 90%, 95%, 96%, 97%, 98%, or 99% complementary to a G6PD mRNA sequence. In some embodiments, the antagomir may be substantially complementary to a G6PD mRNA sequence, that is at least about 95%, 96%, 97%, 98%, or 99% complementary to a target polynucleotide sequence. In other embodiments, the antagomirs are 100% complementary to the G6PD mRNA sequence.

Nucleic Acids

The invention also comprises certain constructs and nucleic acids encoding the complete or portions of an siRNA, shRNA, miRNA or antisense RNA that may be used to reduce or inhibit the level and/or activity of G6PD as described herein. Certain constructs and sequences, including selected G6PD inhibitory sequences such as SEQ ID NO:2, SEQ ID NO:4, SEQ ID NO:5, SEQ ID NO:6, SEQ ID NO:7, SEQ ID NO:9, SEQ ID NO:10, SEQ ID NO:11, SEQ ID NO:12, or combinations thereof, may be useful in certain embodiments.

Preferably, the nucleic acids hybridize under low, moderate or high stringency conditions. A first nucleic acid molecule is "hybridizable" to a second nucleic acid molecule when a single stranded form of the first nucleic acid molecule can anneal to the second nucleic acid molecule under the appropriate conditions of temperature and solution ionic strength (see Sambrook, et al., supra). The conditions of temperature and ionic strength determine the "stringency" of the hybridization. Typical low stringency hybridization conditions include 55° C., 5×SSC, 0.1% SDS and no formamide; or 30% formamide, 5×SSC, 0.5% SDS at 42° C. Typical moderate stringency hybridization conditions are 40% formamide, with 5× or 6×SSC and 0.1% SDS at 42° C. High stringency hybridization conditions are 50% formamide, 5× or 6×SSC at 42° C. or, optionally, at a higher temperature (e.g., 57° C., 59° C., 60° C., 62° C., 63° C., 65° C. or 68° C.). In general, SSC is 0.15M NaCl and 0.015M Na-citrate. Hybridization requires that the two nucleic acids contain complementary sequences, although, depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the higher the stringency under which the nucleic acids may hybridize. For hybrids of greater than 100 nucleotides in length, equations for calculating the melting temperature have been derived (see Sambrook, et al., supra, 9.50-9.51). For hybridization with shorter nucleic acids, e.g., oligonucleotides, the position of mismatches becomes more important, and the length of the oligonucleotide determines its specificity (see Sambrook, et al., supra, 11.7-11.8).

Cardiovascular Diseases

The methods of the present invention may be used to treat a subject having or at risk for cardiovascular disorders or cardiovascular diseases.

Cardiovascular disorders or cardiovascular diseases can include any disorders that affect the cardiovascular system, including the heart and/or blood vessels, such as arteries and veins. Cardiovascular diseases can also include disorders affecting the kidneys. Non-limiting examples of cardiovascular diseases include pulmonary hypertension, pulmonary hypertension-associated heart failure, hypertension, stroke, medial hypertrophy, acute neointimal formation following iatrogenic interventions, atherosclerosis, congestive heart failure, heart failure, myocardial infarction, myocardial ischemia, cardiac ischemia, cardiac hypertrophy, coronary heart disease, cardiac fibrosis, cardiomyopathy, ischemic heart disease, hypertensive heart disease, inflammatory heart disease, valvular heart disease, diseases of the cardiac valves, atherosclerosis, cardiorenal disease, vascular damage, myocardial damage, cardiac valvular disease or other cardiac electrophysiologic abnormalities, hypertension, other cardiac dysfunction, and combinations thereof. Cardiovascular disease can include, but is not limited to, right-sided, left-sided failure or congestive heart failure and could be due to any one of a number of different causes. Any type of cardiovascular disease which includes impaired functioning of either the left or right ventricle is also encompassed herein. In some embodiments, cardiovascular diseases include diabetes mellitus, hyperhomocysteinemia and hypercholesterolemia.

Non-limiting examples of cardiovascular diseases that may be treated by the present composition and method also include angiosarcoma, hemangioscarcoma, Timothy Syndrome, hypertrophic cardiomyopathy, and combinations thereof.

Cardiomyopathies can include, but are not limited to, alcoholic cardiomyopathy, coronary artery disease, congenital heart disease, ischemic cardiomyopathy (ICM), dilated cardiomyopathy (DCM), hypertrophic cardiomyopathy, hypertensive cardiomyopathy, valvular cardiomyopathy, inflammatory cardiomyopathy, diabetic cardiomyopathy, and myocardiodystrophy, as well as other forms of cardiomyopathies.

Pulmonary hypertension includes pulmonary hypertension groups 1-5, including scleroderma, which is a member of group 1 pulmonary hypertension and is an autoimmune condition. (See: Ryan, John J. et al. "The WHO Classification of Pulmonary Hypertension: A Case-Based Imaging Compendium." Pulmonary Circulation 2.1 (2012): 107-121. PMC. Web. 16 Nov. 2016.)

Hypertensive heart diseases can include, but are not limited to, left ventricular hypertrophy, coronary heart disease, heart failure (including congestive), hypertensive cardiomyopathy, cardiac arrhythmias and renal disorders.

Inflammatory heart diseases can include, but are not limited to, endocarditis, inflammatory cardiomegaly and myocarditis.

Combination Therapy

The present composition may be administered alone or in combination with a second agent/treatment method (therapeutic intervention).

Therapeutic interventions that may be used in combination with the present composition or method can include, pharmacologic intervention, devices, surgical intervention, or any combination thereof. Pharmacologic interventions may include, but are not limited to, treatment with diuretics, vasodilators, inotropic agents (i.e., compounds that increase cardiac contractility), ACE inhibitors, beta blockers, neurohumoral blockers (e.g., beta-blockers, angiotensin converting enzyme inhibitors), and aldosterone antagonists (e.g., spironolactone, eplerenone), histone deactylase inhibitors, and erythropoietin. Devices may include, e.g., a bi-ventricular pacemarker, implantable cardioverter-defibrillator (ICD), ventricular assist device (VAD), left ventricular assist device (LVAD), or cardiac resynchronization therapy (CRT). Surgical interventions may include, heart transplantation, artificial heart, etc.

In certain embodiments, therapeutic intervention can be implantation of a medical device or surgical, which includes, for example, preventative, diagnostic or staging, curative and palliative surgery. Surgery may be used in conjunction with other therapies, including one or more other agents as described herein. Such surgical therapeutic agents for vascular and cardiovascular diseases and disorders are well known to those of skill in the art, and may include, but are not limited to, providing a cardiovascular mechanical prosthesis, angioplasty, coronary artery reperfusion, catheter ablation, providing an implantable cardioverter defibrillator to the subject, mechanical circulatory support or a combination thereof. Examples of a mechanical circulatory support that may be used in the present invention comprise an intra-aortic balloon counterpulsation, left ventricular assist device (LVAD) or combinations thereof.

Pharmacologic agents for therapeutic interventions can include, but are not limited to, miRNA based therapeutics (including antisense oligonucleotides), antihyperlipoproteinemic agent, an antiarteriosclerotic agent, an antithrombotic/fibrinolytic agent, a blood coagulant, an antiarrhythmic agent, an antihypertensive agent, a vasopressor, a treatment agent for congestive heart failure, an antianginal agent, an antibacterial agent or a combination thereof. U.S. Patent Application No. 2010/0317713.

An antihyperlipoproteinemic may be an agent that lowers the concentration of one of more blood lipids and/or lipoproteins. Examples of antihyperlipoproteinemics can include but are not limited to, acifran, azacosterol, benfluorex, p-benzalbutyramide, carnitine, chondroitin sulfate, clomestrone, detaxtran, dextran sulfate sodium, 5, 8, 11, 14, 17-eicosapentaenoic acid, eritadenine, furazabol, meglutol, melinamide, mytatrienediol, ornithine, y-oryzanol, pantethine, pentaerythritol tetraacetate, alpha-phenylbutyramide, pirozadil, probucol (lorelco), p-sitosterol, sultosilic acid-piperazine salt, tiadenol, triparanol and xenbucin. In some embodiments, antihyperlipoproteinemic agents can further comprise an aryloxyalkanoicifibric acid derivative, a resin/bile acid sequesterant, an HMG CoA reductase inhibitor, a nicotinic acid derivative, a thyroid hormone or thyroid hormone analog, a miscellaneous agent or a combination thereof.

In another embodiment, administration of an agent that aids in the removal or prevention of blood clots may be combined with administration of a modulator, particularly in treatment of athersclerosis and vasculature (e.g., arterial) blockages. Examples of antithrombotic and/or fibrinolytic agents can include but are not limited to anticoagulants, anticoagulant antagonists, antiplatelet agents, thrombolytic agents, throinbolytic agent antagonists or combinations thereof. Antithrombotic agents that can be included are those that are administered orally, such as, for example, aspirin and warfarin (coumadin).

Anticoagulants can include but are not limited to acenocoumarol, ancrod, anisindione, bromindione, clorindione, coumetarol, cyclocumarol, dextran sulfate sodium, dicumarol, diphenadione, ethyl biscoumacetate, ethylidene dicoumarol, fluindione, heparin, hirudin, lyapolate sodiuim, oxazidione, pentosan polysulfate, phenindione, phenprocoumon, phosvitin, picotamide, tioclomarol and warfarin.

Antiplatelet agents can include but are not limited to aspirin, a dextran, dipyridamole (persantin), heparin, sulfinpyranone (anturane) and ticlopidine (ticlid).

Thrombolytic agents can include but are not limited to tissue plasminogen activator (activase), plasmin, pro-urokinase, urokinase (abbokinase) streptokinase (streptase) and anistreplasel APSAC (eminase).

In one embodiment, the therapeutic intervention is an antiarrhythmic agent.

Antiarrhythmic agents can include, but are not limited to Class I antiarrhythmic agents (sodium channel blockers), Class II antiarrhythmic agents (beta-adrenergic blockers), Class III antiarrhythmic agents (repolarization prolonging drugs), Class IV antiarrhythmic agents (calcium channel blockers) and miscellaneous antiarrhythric agents. Examples of sodium channel blockers can include but are not limited to Class IA, Class IB and Class IC antiarrhythmic agents. Non-limiting examples of Class IA antiarrhythmic agents include disppyramide (norpace), procainamide (pronestyl) and quinidine (quinidex). Examples of Class IB antiarrhythmic agents can include but are not limited to lidocaine (xylocalne), tocamide (tonocard) and mexiletine (mexitil). Examples of Class IC antiarrhythmic agents can include but are not limited to encamide (enkaid) and flecamide (tambocor).

Examples of a beta blocker, otherwise known as a p-adrenergic blocker, a p-adrenergic antagonist or a Class II antiarrhythmic agent, can include but are not limited to acebutolol (sectral), alprenolol, amosulalol, arotinolol, atenolol, befunolol, betaxolol, bevantolol, bisoprolol, bopindolol, bucumolol, bufetolol, bufuralol, bunitrolol, bupranolol, butidrine hydrochloride, butofilolol, carazolol, carteolol, carvedilol, celiprolol, cetamolol, cloranolol, dilevalol, epanolol, esmolol (brevibloc), indenolol, labetalol, levobunolol, mepindolol, metipranolol, metoprolol, moprolol, nadolol, nadoxolol, nifenalol, nipradilol, oxprenolol, penbutolol, pindolol, practolol, pronethalol, propanolol (inderal), sotalol (betapace), sulfinalol, talinolol, tertatolol, timolol, toliprolol and xibinolol. In some embodiments, the beta blocker can comprise an aryloxypropanolamine derivative. Examples of aryloxypropanolamine derivatives can include but are not limited to acebutolol, alprenolol, arotinolol, atenolol, betaxolol, bevantolol, bisoprolol, bopindolol, bunitrolol, butofilolol, carazolol, carteolol, carvedilol, celiprolol, cetamolol, epanolol, indenolol, mepindolol, metipranolol, metoprolol, mrnoprolol, nadolol, nipradilol, oxprenolol, penbutolol, pindolol, propanolol, talinolol, tertatolol, tinolol and toliprolol.

Examples of agents that prolong repolarization, also known as a Class III antiarrhythmic agent, can include but are not limited to include amiodarone (cordarone) and sotalol (betapace).

Examples of a calcium channel blocker, otherwise known as a Class IV antiarrhythmic agent, can include but are not limited to an arylalkylamine (e.g., bepridile, diltiazem, fendiline, gallopamil, prenylamine, terodiline, verapamil), a dihydropyridine derivative (felodipine, isradipine, nicardipine, nifedipine, nimodipine, nisoldipine, nitrendipine) a piperazinde derivative (e.g., cinnarizine, flunarizine, lidoflazine) or a micellaneous calcium channel blocker such as bencyclane, etafenone, magnesium, mibefradil or perhexyline. In some embodiments, a calcium channel blocker comprises a long-acting dihydropyridine (nifedipine-type) calcium antagonist.

Examples of antihypertensive agents can include but are not limited to sympatholytic, alpha/beta blockers, alpha blockers, anti-angiotensin II agents, beta blockers, calcium channel blockers, vasodilators and miscellaneous antihypertensives.

Examples of an alpha blocker, also known as an α-adrenergic blocker or an α-adrenergic antagonist, can include but are not limited to, amosulalol, arotinolol, dapiprazole, doxazosin, ergoloid mesylates, fenspiride, indoramin, labetalol, nicergoline, prazosin, terazosin, tolazoline, trimazosin and yohimbine. In certain embodiments, an alpha blocker may comprise a quinazoline derivative. Quinazoline derivatives can include but are not limited to alfuzosin, bunazosin, doxazosin, prazosin, terazosin and trimazosin. The antihypertensive agent may be both an alpha and beta adrenergic antagonist. Examples of an alpha/beta blocker can include but are not limited to labetalol (normodyne, trandate).

Examples of anti-angiotensin II agents can include but are not limited to angiotensin converting enzyme inhibitors and angiotensin II receptor antagonists. Angiotensin converting enzyme inhibitors (ACE inhibitors) can include but are not limited to alacepril, enalapril (vasotec), captopril, cilazapril, delapril, enalaprilat, fosinopril, lisinopril, moveltopril, perindopril, quinapril and ramipril. Examples of an angiotensin II receptor blocker, also known as an angiotensin II receptor antagonist, an ANG receptor blocker or an ANG-II type-I receptor blocker (ARBS), include but are not limited to angiocandesartan, eprosartan, irbesartan, losartan and valsartan.

Examples of a sympatholytic include a centrally acting sympatholytic or a peripherially acting sympatholytic. Examples of a centrally acting sympatholytic, also known as a central nervous system (CNS) sympatholytic, can include but are not limited to clonidine (catapres), guanabenz (wytensin) guanfacine (tenex) and methyldopa (aldomet).

Examples of a peripherally acting sympatholytic can include but are not limited to a ganglion blocking agent, an adrenergic neuron blocking agent, beta-adrenergic blocking agent or an alphal-adrenergic blocking agent. Examples of a ganglion blocking agent include mecamylamine (inversine) and trimethaphan (arfonad). Examples of an adrenergic neuron blocking agent can include but are not limited to guanethidine (ismelin) and reserpine (serpasil).

Examples of a beta-adrenergic blocker can include but are not limited to acenitolol (sectral), atenolol (tenormin), betaxolol (kerlone), carteolol (cartrol), labetalol (normodyne, trandate), metoprolol (lopressor), nadanol (corgard), penbutolol (levatol), pindolol (visken), propranolol (inderal) and timolol (blocadren).

Examples of alphal-adrenergic blocker can include but are not limited to prazosin (minipress), doxazocin (cardura) and terazosin (hytrin).

The therapeutic intervention can also comprise a vasodilator (e.g., a cerebral vasodilator, a coronary vasodilator or a peripheral vasodilator). In other embodiments, a vasodilator comprises a coronary vasodilator. Examples of a coronary vasodilator include but are not limited to amotriphene, bendazol, benfurodil hemisuccinate, benziodarone, chloracizine, chromonar, clobenfurol, clonitrate, dilazep, dipyridamole, droprenilamine, efloxate, erythrityl tetranitrane, etafenone, fendiline, floredil, ganglefene, herestrol bis(p-dinoeylaminoethyl ether), hexobendine, itramin tosylate, khellin, lidoflanine, mannitol hexanitrane, medibazine, nicorglycerin, pentaerythritol tetranitrate, pentrinitrol, perhexyline, pimefyiline, trapidil, tricromyl, trimeG6PDidine, troInitrate phosphate and visnadine. In some embodiments, a vasodilator can comprise a chronic therapy vasodilator or a hypertensive emergency vasodilator. Examples of a chronic therapy vasodilator can include but are not limited to hydralazine (apresoline) and minoxidil (loniten). Examples of a hypertensive emergency vasodilator can include but are not limited to nitroprusside (nipride), diazoxide (hyperstat IV), hydralazine (apresoline), minoxidil (loniten) and verapamil.

Examples of antihypertensives can also include, but are not limited to, ajmaline, gamma-amino butyric acid, bufeniode, cicletainine, ciclosidomine, a cryptenamine tannate, fenoldopam, flosequinan, ketanserin, mebutamate, mecamylamine, methyldopa, methyl 4-pyridyl ketone thiosemicarbazone, muzo limine, pargyline, pempidine, pinacidil, piperoxan, primaperone, a protoveratrine, raubasine, rescimetol, rilmenidene, saralasin, sodium nitrorusside, ticrynafen, trimethaphan camsylate, tyrosinase and urapidil.

In certain embodiments, an antihypertensive can comprise an arylethanolamine derivative, a benzothiadiazine derivative, a N-carboxyalkyl(peptide/lactam) derivative, a dihydropyridine derivative, a guanidine derivative, a hydrazines/phthalazine, an imidazole derivative, a quaternary ammoniam compound, a reserpine derivative or a suflonamide derivative. Examples of arylethanolamine derivatives can include but are not limited to amosulalol, bufuralol, dilevalol, labetalol, pronethalol, sotalol and sulfinalol. Examples of benzothiadiazine derivatives can include but are not limited to althizide, bendroflumethiazide, benzthiazide, benzylhydrochlorothiazide, buthiazide, chlorothiazide, chlorthalidone, cyclopenthiazide, cyclothiazide, diazoxide, epithiazide, ethiazide, fenquizone, hydrochlorothizide, hydroflumethizide, methyclothiazide, meticrane, metolazone, paraflutizide, polythizide, tetrachlormethiazide and trichlormethiazide. Examples of N-carboxyalkyl(peptide/lactam) derivatives can include but are not limited to alacepril, captopril, cilazapril, delapril, enalapril, enalaprilat, fosinopril, lisinopril, moveltipril, perindopril, quinapril and ramipril. Examples of dihydropyridine derivatives can include but are not limited to amlodipine, felodipine, isradipine, nicardipine, nifedipine, nilvadipine, nisoldipine and nitrendipine. Examples of guanidine derivatives can include but are not limited to bethanidine, debrisoquin, guanabenz, guanacline, guanadrel, guanazodine, guanethidine, guanfacine, guanochlor, guanoxabenz and guanoxan. Examples of hydrazines/phthalazines can include but are not limited to budralazine, cadralazine, dihydralazine, endralazine, hydracarbazine, hydralazine, pheniprazine, pildralazine and todralazine. Examples of imidazole derivatives can include but are not limited to clonidine, lofexidine, phentolamine, tiamenidine and tolonidine. Examples of quaternary ammonium compounds can include but are not limited to azamethonium bromide, chlorisondamine chloride, hexamethonium, pentacynium bis(methylsulfate), pentamethoniumi bromide, pentolinium tartrate, phenactropiniutm chloride and trimethidinium methosulfate. Examples of reserpine derivatives can include but are not limited to bietaserpine, deserpidine, rescinnamine, reserpine and syrosingopine. Examples of sulfonamide derivatives can include but are not limited to ambuside, clopamide, furosemide, indapamide, quinethazone, trip amide and xipamide.

Examples of agents for the treatment of congestive heart failure can include but are not limited to anti-angiotensin II agents, afterload-preload reduction treatment, diuretics and inotropic agents.

Examples of a diuretic can include but are not limited to a thiazide or benzothiadiazine derivative (e.g., althiazide, bendroflumethazide, benzthiazide, benzylhydrochiorchlorothiazide, buthiazide, chlorothiazide, chlorothiazide, chlorthalidone, cyclopenthiazide, epithiazide, ethiazide, ethiazide, fenquizone, hydrochlorothiazide, hydroflumethiazide, methyclothiazide, meticrane, metolazone, paraflutizide, polythizide, tetrachloromethiazide, trichlormethiazide), an organomercurial (e.g., chlormerodrin, meralluride, mercamnphamide, mercaptomerin sodium, mercumallylic acid, mercumatilin dodium, mercurous chloride, mersalyl), a pteridine (e.g., furtherene, triamterene), purines (e.g., acefylline, 7-morpholinomethyltheophylline, pamobrom, protheobromine, theobromine), steroids including aldosterone antagonists (e.g., canrenone, oleandrin, spironolactone), a sulfonamide derivative (e.g., aceG6PDolamide, ambuside, azosemide, bumetanide, buG6PDolamide, chloraminophenami de, clofenamide, clopamide, clorexolone, diphenylmethane-4,4'-disulfonamide, disulfamide, ethoxzolamide, furosemide, indapamide, mefruside, methazolamide, piretanide, quinethazone, torasemide, trip amide, xipamide), a uracil (e.g., aminometradine, amisometradine), a potassium sparing antagonist (e.g., amiloride, triamterene) or a miscellaneous diuretic such as aminozine, arbutin, chlorazanil, ethacrynic acid, etozolin, hydracarbazine, isosorbide, mannitol, metochalcone, muzo limine, perhexyline, ticmafen and urea.

Examples of a positive inotropic agent, also known as a cardiotonic, can include but are not limited to acefylline, an acetyldigitoxin, 2-amino-4-picoline, aminone, benfurodil hemisuccinate, bucladesine, cerberosine, camphotamide, convallatoxin, cymarin, denopamine, deslanoside, digitalin, digitalis, digitoxin, digoxin, dobutamine, dopamine, dopexamine, enoximone, erythrophleine, fenalcomine, gitalin, gitoxin, glycocyamine, heptaminol, hydrastinine, ibopamine, a lanatoside, metamivam, milrinone, nerifolin, oleandrin, ouabain, oxyfedrine, prenalterol, proscillaridine, resibufogenin, scillaren, scillarenin, strphanthin, sulmazole, theobromine and xamoterol. In some embodiments, an intropic agent is a cardiac glycoside, a beta-adrenergic agonist or a phosphodiesterase inhibitor. Examples of a cardiac glycoside can include but are not limited to digoxin (lanoxin) and digitoxin (crystodigin). Examples of a .beta.-adrenergic agonist include but are not limited to albuterol, bambuterol, bitolterol, carbuterol, clenbuterol, clorprenaline, denop amine, dioxethedrine, dobutamine (dobutrex), dopamine (intropin), dopexamine, ephedrine, etafedrine, ethylnorepinephrine, fenoterol, formoterol, hexoprenaline, ibopamine, isoetharine, isoproterenol, mabuterol, metaproterenol, methoxyphenamine, oxyfedrine, pirbuterol, procaterol, protokylol, reproterol, rimiterol, ritodrine, soterenol, terbutaline, tretoquinol, tulobuterol and xamoterol. Examples of a phosphodiesterase inhibitor can include but are not limited to aminone (inocor).

Antianginal agents may comprise organonitrates, calcium channel blockers, beta blockers and combinations thereof. Examples of organonitrates, also known as nitrovasodilators, can include but are not limited to nitroglycerin (nitrobid, nitrostat), isosorbide dinitrate (isordil, sorbitrate) and amyl nitrate (aspirol, vaporole).

Endothelin (ET) is a 21-amino acid peptide that has potent physiologic and pathophysiologic effects that appear to be involved in the development of heart failure. The effects of ET are mediated through interaction with two classes of cell surface receptors. Inhibiting the ability of ET to stimulate cells involves the use of agents that block the interaction of ET with its receptors. Examples of endothelin receptor antagonists (ERA) can include but are not limited to Bosentan, Enrasentan, Ambrisentan, Darusentan, Tezosentan, Atrasentan, Avosentan, Clazosentan, Edonentan, sitaxsentan, TBC 3711, BQ 123, and BQ 788.

Histone deacetylase inhibitors that appear to have beneficial effects the treatment of pulmonary hypertension. Examples of histone deacetylase inhibitors can include but are not limited to valproic acid and suberoylanilide hydroxamic acid.

Evidence of therapeutic efficacy may be specific to the cardiovascular disease being treated and can include evidence well known in the art. For example, evidence of therapeutic efficacy can include but is not limited to improvement or alleviation of one or more symptoms of cardiac hypertrophy, heart failure, or myocardial infarction in the subject, or in the delay in the transition from cardiac hypertrophy to heart failure. The one or more improved or alleviated symptoms can include, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life, and decreased disease related morbidity or mortality. Further, therapeutic efficacy can also include general improvements in the overall health of the patient, such as but not limited to enhancement of patient life quality, increase in predicted survival rate, decrease in depression or decrease in rate of recurrence of the indication (Physicians' Desk Reference (2010).

Efficacy of a therapeutic intervention can also include evaluating or monitoring for the improvement of one or more symptoms of cardiac hypertrophy, heart failure, or myocardial infarction in the subject, or for the delay in the transition from cardiac hypertrophy to heart failure. The one or more improved symptoms may include, for example, increased exercise capacity, increased cardiac ejection volume, decreased left ventricular end diastolic pressure, decreased pulmonary capillary wedge pressure, increased cardiac output, increased cardiac index, lowered pulmonary artery pressures, decreased left ventricular end systolic and diastolic dimensions, decreased cardiac fibrosis, decreased collagen deposition in cardiac muscle, decreased left and right ventricular wall stress, decreased wall tension, increased quality of life and decreased disease related morbidity or mortality. The measured levels of plasma miRNAs may serve as a surrogate marker for efficacy of the therapeutic intervention.

Definitions

So that the invention may be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Activation," "stimulation," and "treatment," as it applies to cells or to receptors, may have the same meaning, e.g., activation, stimulation, or treatment of a cell or receptor with a ligand, unless indicated otherwise by the context or explicitly. "Ligand" encompasses natural and synthetic ligands, e.g., cytokines, cytokine variants, analogues, muteins, and binding compounds derived from antibodies. "Ligand" also encompasses small molecules, e.g., peptide mimetics of cytokines and peptide mimetics of antibodies. "Activation" can refer to cell activation as regulated by internal mechanisms as well as by external or environmental factors. "Response," e.g., of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming.

"Activity" of a molecule may describe or refer to the binding of the molecule to a ligand or to a receptor, to catalytic activity; to the ability to stimulate gene expression or cell signaling, differentiation, or maturation; to antigenic activity, to the modulation of activities of other molecules, and the like. "Activity" of a molecule may also refer to activity in modulating or maintaining cell-to-cell interactions, e.g., adhesion, or activity in maintaining a structure of a cell, e.g., cell membranes or cytoskeleton. "Activity" can also mean specific activity, e.g., [catalytic activity]/[mg protein], or [immunological activity]/[mg protein], concentration in a biological compartment, or the like. "Activity" may refer to modulation of components of the innate or the adaptive immune systems.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. "Administration" and "treatment" can refer, e.g., to therapeutic, pharmacokinetic, diagnostic, research, and experimental methods. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell. The term "subject" includes any organism, preferably an animal, more preferably a mammal (e.g., rat, mouse, dog, cat, rabbit) and most preferably a human, including a human patient.

"Treat" or "treating" refers to administering a therapeutic agent, such as a composition containing any of the liver targeted viral vectors, RNAi, shRNA or other G6PD inhibitors, or similar compositions described herein, internally or externally to a subject or patient having one or more disease symptoms, or being suspected of having a disease or being at elevated at risk of acquiring a disease, for which the agent has therapeutic activity. Gene editing technology such as CRISPR/cas9 methods may also be utilized to carry out liver specific reduction of G6PD. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to factors such as the disease state, age, and weight of the patient, and the ability of the drug to elicit a desired response in the subject whether a disease symptom has been alleviated can be assessed by any clinical measurement typically used by physicians or other skilled healthcare providers to assess the severity or progression status of that symptom. While an embodiment of the present invention (e.g., a treatment method or article of manufacture) may not be effective in alleviating the target disease symptom(s) in every subject, it should alleviate the target disease symptom(s) in a statistically significant number of subjects as determined by any statistical test known in the art such as the Student's t-test, the $chi^2$-test, the U-test according to Mann and Whitney, the Kruskal-Wallis test (H-test), Jonckheere-Terpstra-test and the Wilcoxon-test.

"Treatment," as it applies to a human, veterinary, or research subject, refers to therapeutic treatment, prophylactic or preventative measures, to research and diagnostic applications. "Treatment" as it applies to a human, veterinary, or research subject, or cell, tissue, or organ, encompasses transfection of any of the viral vectors, delivery of RNAi, shRNA or other G6PD inhibitors, or similar compositions, including gene editing technology such as CRISPR/cas9 methods, which may be utilized to carry out any tissue-specific or general reduction of G6PD, or related methods described herein as applied to a human or animal subject, a cell, tissue, physiological compartment, or physiological fluid.

"Isolated nucleic acid molecule" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences may include, in addition to the specified sequences, coding sequences for up to ten or even up to twenty or more other proteins or portions or fragments thereof, or may include operably linked regulatory sequences that control expression of the coding region of the recited nucleic acid sequences, and/or may include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

With respect to cells, the term "isolated" refers to a cell that has been isolated from its natural environment (e.g., from a tissue or subject). The term "cell line" refers to a population of cells capable of continuous or prolonged growth and division in vitro. Often, cell lines are clonal populations derived from a single progenitor cell. It is further known in the art that spontaneous or induced changes can occur in karyotype during storage or transfer of such clonal populations. Therefore, cells derived from the cell line referred to may not be precisely identical to the ancestral cells or cultures, and the cell line referred to includes such variants. As used herein, the terms "recombinant cell" refers to a cell into which an exogenous DNA segment, such as DNA segment that leads to the transcription of a biologically-active polypeptide or production of a biologically active nucleic acid such as RNA, has been introduced.

The term "vector" includes any genetic element, such as a plasmid, phage, transposon, cosmid, chromosome, artificial chromosome, virus, virion, etc., which is capable of replication when associated with the proper control elements and which can transfer gene sequences between cells. Thus, the term includes cloning and expression vehicles, as well as viral vectors. In some embodiments, useful vectors are contemplated to be those vectors in which the nucleic acid segment to be transcribed is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned," "operatively linked," "under control," or "under transcriptional control" means that the promoter is in the correct location and orientation in relation to the nucleic acid to control RNA polymerase initiation and expression of the gene. The term "expression vector or construct" means any type of genetic construct containing a nucleic acid in which part or all of the nucleic acid encoding sequence is capable of being transcribed. In some embodiments, expression includes transcription of the nucleic acid, for example, to generate a biologically-active polypeptide product or inhibitory RNA (e.g., shRNA, miRNA) from a transcribed gene.

Pharmaceutical Compositions and Administration

To prepare pharmaceutical or sterile compositions of the compositions of the present invention, the viral vectors, RNAi, shRNA or other G6PD inhibitors, or similar compositions may be admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents may be prepared by mixing with acceptable carriers, excipients, or stabilizers in the form of, e.g., lyophilized powders, slurries, amorphous solution or solid, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the therapeutic compositions, administered alone or in combination with another agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). In particular aspects, therapeutic compositions exhibiting high therapeutic indices are desirable. The data obtained from these cell culture assays and animal studies can be used in formulating a range of dosage for use in human. The dosage of such compounds lies preferably within a range of circulating concentrations that include the $ED_{50}$ with little or no toxicity. The dosage may vary within this range depending upon the dosage form employed and the route of administration.

In an embodiment of the invention, a composition of the invention is administered to a subject in accordance with the Physicians' Desk Reference 2003 (Thomson Healthcare; 57th edition (Nov. 1, 2002)).

The mode of administration can vary. Suitable routes of administration include intranasal, nasal, oral, rectal, transmucosal, intestinal, parenteral; intramuscular, subcutaneous, intradermal, intramedullary, intrathecal, direct intraventricular, intravenous, intraperitoneal, intraocular, inhalation, insufflation, topical, cutaneous, transdermal, or intra-arterial.

In particular embodiments, the composition or therapeutic can be administered by an invasive route such as by injection (see above). In further embodiments of the invention, the composition, therapeutic, or pharmaceutical composition thereof, is administered intravenously, subcutaneously, intramuscularly, intraarterially, intra-articularly (e.g. in arthritis joints), intratumorally, or by inhalation, aerosol delivery. Administration by non-invasive routes (e.g., orally; for example, in a pill, capsule or tablet) is also within the scope of the present invention.

Compositions can be administered with medical devices known in the art. For example, a pharmaceutical composition of the invention can be administered by injection with a hypodermic needle, including, e.g., a prefilled syringe or autoinjector.

The pharmaceutical compositions of the invention may also be administered with a needleless hypodermic injection device; such as the devices disclosed in U.S. Pat. No. 6,620,135; 6,096,002; 5,399,163; 5,383,851; 5,312,335; 5,064,413; 4,941,880; 4,790,824 or 4,596,556.

Alternately, one may administer the viral vectors, RNAi, shRNA or other G6PD inhibitors, or related compound in a local rather than systemic manner, for example, via injection of directly into the desired target site, often in a depot or sustained release formulation. Furthermore, one may administer the composition in a targeted drug delivery system, for example, in a liposome coated with a tissue-specific antibody, targeting, for example, the liver, and more specifically hepatocytes. The liposomes will be targeted to and taken up selectively by the desired tissue. Also included in a targeted drug delivery system is nanoparticle specific nasal or cardiac delivery of the viral vectors, RNAi, shRNA or other G6PD inhibitors, or G6PD-based compound, alone or in combination with an Ihh RNAi construct or similar inhibitors. A summary of various delivery methods and techniques of siRNA administration in ongoing clinical trials is provided in Zuckerman and Davis 2015; Nature Rev. Drug Discovery, Vol. 14: 843-856, December 2015.

The present composition can also comprise a delivery vehicle, including liposomes, for administration to a subject, carriers and diluents and their salts, and/or can be present in pharmaceutically acceptable formulations. For example, methods for the delivery of nucleic acid molecules are described in Akhtar et al., 1992, Trends Cell Bio., 2, 139; DELIVERY STRATEGIES FOR ANTISENSE OLIGONUCLEOTIDE THERAPEUTICS, ed. Akbtar, 1995, Maurer et al., 1999, Mol. Membr. Biol., 16, 129-140; Hofland and Huang, 1999, Handb. Exp. Pharmacol., 137, 165-192; and Lee et al., 2000, ACS Symp. Ser., 752, 184-192. U.S. Pat. No. 6,395,713 and PCT Publication No. WO 94/02595 further describe the general methods for delivery of nucleic acid molecules. These protocols can be utilized for the delivery of virtually any nucleic acid molecule.

The present composition can be administered to a desired target by a variety of methods known to those of skill in the art, including, but not restricted to, encapsulation in liposomes, by iontophoresis, or by incorporation into other vehicles, such as hydrogels, cyclodextrins, biodegradable nanocapsules, and bioadhesive microspheres, or by proteinaceous vectors (see PCT Publication No. WO 00/53722). Alternatively, the therapeutic/vehicle combination is locally delivered by direct injection or by use of an infusion pump. Direct injection of the composition, whether subcutaneous, intramuscular, or intradermal, can take place using standard needle and syringe methodologies, or by needle-free technologies such as those described in Conry et al., 1999, *Clin. Cancer Res.*, 5, 2330-2337 and PCT Publication No. WO 99/3 1262.

Therapeutic compositions comprising surface-modified liposomes containing poly(ethylene glycol) lipids (PEG-modified, or long-circulating liposomes or stealth liposomes) may also be suitably employed in the methods of the invention. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601-2627; Ishiwata et al., *Chem. Pharm. Bull.* 1995, 43, 1005-1011). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864-24870; PCT Publication No. WO 96/10391; PCT Publication No. WO 96/10390; and PCT Publication No. WO 96/10392). Long-circulating liposomes are also likely to protect drugs from nuclease degradation to a greater extent compared to cationic liposomes, based on their ability to avoid accumulation in metabolically aggressive MPS tissues such as the liver and spleen.

The administration regimen depends on several factors, including the serum or tissue turnover rate of the therapeutic composition, the level of symptoms, and the accessibility of the target cells in the biological matrix. Preferably, the administration regimen delivers sufficient therapeutic composition to effect improvement in the target disease state, while simultaneously minimizing undesired side effects. Accordingly, the amount of biologic delivered depends in part on the particular therapeutic composition and the severity of the condition being treated.

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent.

As used herein, "inhibit" or "treat" or "treatment" includes a postponement of development of the symptoms associated with a disorder and/or a reduction in the severity of the symptoms of such disorder. The terms further include ameliorating existing uncontrolled or unwanted symptoms, preventing additional symptoms, and ameliorating or preventing the underlying causes of such symptoms. Thus, the terms denote that a beneficial result has been conferred on a vertebrate subject with a disorder, disease or symptom, or with the potential to develop such a disorder, disease or symptom.

As used herein, the terms "therapeutically effective amount", "therapeutically effective dose" and "effective amount" refer to an amount of a viral vector, RNAi, shRNA or other G6PD inhibitors or inhibitor compound of the invention that, when administered alone or in combination with an additional therapeutic agent to a cell, tissue, or subject, is effective to cause a measurable improvement in one or more symptoms of a disease or condition or the progression of such disease or condition. A therapeutically effective dose further refers to that amount of the compound sufficient to result in at least partial amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

Kits

The present invention also provides kits comprising the components of the combinations of the invention in kit form. A kit of the present invention includes one or more components including, but not limited to, the viral vectors, RNAi, shRNA or other G6PD inhibitors, or G6PD-based inhibitor compounds, as discussed herein, in association with one or more additional components including, but not limited to a pharmaceutically acceptable carrier and/or a chemotherapeutic agent, as discussed herein. The viral vectors, RNAi, shRNA or other G6PD inhibitors, or G6PD-based inhibitor compounds, composition and/or the therapeutic agent can be formulated as a pure composition or in combination with a pharmaceutically acceptable carrier, in a pharmaceutical composition.

Kits may also include primers, buffers, and probes along with instructions for determining elevated levels of nucleic acid, proteins, or protein fragments of G6PD, or any combination thereof.

In one embodiment, a kit includes the viral vectors, RNAi, shRNA, or other G6PD inhibitors, or G6PD-based inhibitor compounds/composition of the invention or a pharmaceutical composition thereof in one container (e.g., in a sterile glass or plastic vial) and a pharmaceutical composition thereof and/or a chemotherapeutic agent in another container (e.g., in a sterile glass or plastic vial).

In another embodiment of the invention, the kit comprises a combination of the invention, including the viral vectors, RNAi, shRNA or other G6PD inhibitors, or G6PD-based inhibitor compounds, along with a pharmaceutically acceptable carrier, optionally in combination with one or more therapeutic agent components formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of the invention may be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

General Methods

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning*, $3^{rd}$ ed., Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, NY, pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protocols in Immunology*, Vol. 1, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Examples

We propose that increased G6PD activity promotes a synthetic PASMC phenotype. In HPH, these PASMC will contribute to medial thickening of muscular PA and neo-muscularization of arterioles. Higher G6PD activity in lungs of PAH mice will play a major role in activating endothelial cells and/or fibroblasts as well as switching PASMC phenotype, and these cells altogether will mediate neomuscularization of arterioles and formation of complex cellular and fibrotic neointimal and plexiform lesions in distal PA.
Remodeling and Phenotype of Vascular Smooth Muscle Cell (VSMC)

Adult VSMC may exhibit a contractile "differentiated" or synthetic "dedifferentiated" phenotype (1, 8, 9, 15). These phenotypes are not necessarily stable, irreversible or mutually exclusive (15, 18). Contractile phenotype of VSMC is required for proper functionality of blood vessels i.e. to contract and relax in response to sympathetic stimuli or to nitric oxide, respectively. It is well known that VSMCs switch from a contractile to synthetic phenotype in response to injury or chemical stimuli. This phenotypic switching contributes to vascular remodeling associated with medial hypertrophy, acute neointimal formation following iatrogenic interventions, atherosclerosis, hypertension, and pulmonary hypertension (1, 8, 9).

RNAi Injections and Intra-Nasal Delivery Spray to Knockdown G6PD Expression

The G6PD-specific siRNA gene sequence (CAACAUCGCCUGCGUUAUC; SEQ ID NO: 2) that specifically and efficaciously downregulated G6PD (based on our preliminary results) and a scramble sequence (negative control) that can be produced by the short hairpin (sh) RNA was produced. PASM cells cultured in a 12-well plate were transfected for 72 h with 100 nmol/l shRNA targeting G6PD using lipid-based and nano-particle based transfection system. Control experiments were performed using a nontargeting/scrambled (NT) shRNA (negative control).

In FIG. 1, Control mice were treated with CYPKO and CYPKO-IT-shG6PD-GFP, respectively. FIG. 1 shows distribution of Evan blue and expression of GFP-tagged CYPKO-IT-shG6PD in mice lungs.

In FIGS. 2A-2F, pulmonary hypertension (PH) was induced by exposing mice to 10% 02. Control and PH mice were treated with CYPKO and CYPKO-IT-shG6PD, respectively. FIG. 2A mice were treated by intra-tracheal spray (25 µl of 100 ng CYPKO and CYPKO-IT-shG6PD, respectively) once per week for two weeks. FIG. 2B shows that CYPKO-IT-shG6PD decreased G6PD activity to control levels. FIG. 2C shows that CYPKO-IT-shG6PD decreased reactive oxygen species (ROS). FIG. 2D is an H&E staining showing that pulmonary artery remodeling and occlusive lesion in CYPKO were decreased by CYPKO-IT-shG6PD treatment. FIGS. 2E-2F show that the number of remodeled pulmonary arteries with medial wall thickening in CYPKO mice was decreased by CYPKO-IT-shG6PD treatment.

In FIGS. 3A-3G, pulmonary hypertension (PH) was induced by exposing mice to 10% 02. Control and PH mice were treated with CYPKO and CYPKO-IT-shG6PD, respectively, for 2 weeks. CYPKO-IT-shG6PD treatment decreased pulmonary resistance as determined by PAAT-to-ET (FIGS. 3A-3B), right ventricle (RV) hypertrophy as determined by RV-to-left ventricle+septum ratio (FIG. 3C), arterial elastance (FIG. 3D), total peripheral resistance (FIG. 3E), LV stiffness (FIG. 3F), and increased cardiac index (CI) (FIG. 3G).

In FIGS. 4A-B, rat pulmonary artery smooth muscle cells were cultured in 15% DMEM for 48 hr. Cells were then transfected with G6PD-siRNA#1 and G6PD-siRNA#2, respectively (0.5 and 1.0 µl=50 ng and 100 ng, respectively) and subjected to hypoxia (1% 02) for 72 hr. G6PD-siRNA#2 treatment significantly down-regulated G6PD protein expression as compared to untransfected (UT), non-targeting (NT), and G6PD-siRNA#1 (FIG. 4A). Similarly, G6PD-siRNA#2 significantly down-regulated the expression of replication and cell cycle proteins such as, polymerase delta (FIG. 4B-panel 3), cyclin E1 (FIG. 4B-panel 4), and cyclin B1 (FIG. 4B-panel 5). GAPDH was used as a loading control.

Sequences

Human G6PD 545-cDNA Sequence-SEQ ID NO: 1: [(NM_000402.3); CDs = 149-1786]

```
149    at gggccggcgg ggctcagccc ccggaaacgg 181    tcgtacactt cggggctgcg agcgcggagg gcgacgacga cgaagcgcag acagcgtcat 241    ggcagagcag gtggccctga gccggaccca ggtgtgcggg atcctgcggg aagagctttt 301    ccagggcgat gccttccatc agtcggatac acacatattc atcatcatgg gtgcatcggg 361    tgacctggcc aagaagaaga tctaccccac catctggtgg ctgttccggg atggccttct
```

| Sequences |
|---|
| 421    gcccgaaaac accttcatcg tgggctatgc ccgttcccgc ctcacagtgg ctgacatccg |
| 481    caaacagagt gagcccttct tcaaggccac cccagaggag aagctcaagc tggaggactt |
| 541    ctttgcccgc aactcctatg tggctggcca gtacgatgat gcagcctcct accagcgcct |
| 601    caacagccac atgaatgccc tccacctggg gtcacaggcc aaccgcctct tctacctggc |
| 661    cttgccccg accgtctacg aggccgtcac caagaacatt cacgagtcct gcatgagcca |
| 721    gataggctgg aaccgcatca tcgtggagaa gcccttcggg agggacctgc agagctctga |
| 781    ccggctgtcc aaccacatct cctccctgtt ccgtgaggac cagatctacc gcatcgacca |
| 841    ctacctgggc aaggagatgg tgcagaacct catggtgctg agatttgcca acaggatctt |
| 901    cggccccatc tggaaccggg acaacatcgc ctgcgttatc ctcaccttca aggagcccct |
| 961    tggcactgag ggtcgcgggg gctatttcga tgaatttggg atcatccggg acgtgatgca |
| 1021   gaaccaccta ctgcagatgc tgtgtctggt ggccatggag aagcccgcct ccaccaactc |
| 1081   agatgacgtc cgtgatgaga aggtcaaggt gttgaaatgc atctcagagg tgcaggccaa |
| 1141   caatgtggtc ctgggccagt acgtggggaa ccccgatgga gagggcgagg ccaccaaagg |
| 1201   gtacctggac gaccccacgg tgccccgcgg gtccaccacc gccactttg cagccgtcgt |
| 1261   cctctatgtg gagaatgaga ggtgggatgg ggtgcccttc atcctgcgct gcggcaaggc |
| 1321   cctgaacgag cgcaaggccg aggtgaggct gcagttccat gatgtggccg gcgacatctt |
| 1381   ccaccagcag tgcaagcgca acgagctggt gatccgcgtg cagcccaacg aggccgtgta |
| 1441   caccaagatg atgaccaaga agccgggcat gttcttcaac cccgaggagt cggagctgga |
| 1501   cctgaccta ggcaacagat acaagaacgt gaagctccct gacgcctacg agcgcctcat |
| 1561   cctggacgtc ttctgcggga gccagatgca cttcgtgcgc agcgacgagc tccgtgaggc |
| 1621   ctggcgtatt ttcaccccac tgctgcacca gattgagctg gagaagccca gcccatccc |
| 1681   ctatatttat ggcagccgag gccccacgga ggcagacgag ctgatgaaga gagtgggttt |
| 1741   ccagtatgag ggcacctaca agtgggtgaa ccccacaag ctctga | shRNA Sequence used for designing the CYPKO-IT-shG6PD-GFP packaged in the *adenovirus* (See FIGS. 2-3): Sense (SEQ ID NO: 2) 5' CAACAUCGCCUGCGUUAUC 3' (corresponds to nucleotide positions 922-940 of SEQ ID NO. 1)

First ninety nucleotides of human G6PD545-cDNA (SEQ ID NO. 1): (SEQ ID NO. 3)
5'ATGGGCCGGCGGGGCTCAGCCCCCGGAAACGGTCGTACACTTCGGGGCTGCGAGC
GCGGAGGGCGACGACGACGAAGCGCAGACAGCGTC 3' siRNA sequences used in FIG. 4A-B:
siRNA#1:
Sense (SEQ ID NO. 4) 5'CGGAAACGGUCGUACACUUCG 3'

Antisense (SEQ ID NO. 5) 5'CGAAGUGUACGACCGUUUCCG 3' siRNA#2:
Sense (SEQ ID NO. 6) 5' CGACGAAGCGCAGACAGCGUC 3'

Antisense (SEQ ID NO. 7) 5'GACGCUGUCUGCGCUUCGUCG3'

Oligo Design for exemplary shRNA:
Sense-sequence + NNNNNNNNN/UUCAAGAGA + Antisense-sequence + UUUUUU
                Loop Sequence                              Termination Exemplary Stem loop structure sequence (SEQ ID NO: 8): UUCAAGAGA
G6PD545-shRNA# 1 sequence: (SEQ ID NO. 9)
5' CGGAAACGGUCGUACACUUCG NNNNNNNNN CGAAGUGUACGACCGUUUCCG 3'

(SEQ ID NO. 10)
5' CGGAAACGGUCGUACACUUCG UUCAAGAGA CGAAGUGUACGACCGUUUCCG 3'

-continued

Sequences

G6PD545-shRNA# 2 sequence: (SEQ ID NO. 11)
5' CGACGAAGCGCAGACAGCGUC NNNNNNNNN GACGCUGUCUGCGCUUCGUCG 3'

(SEQ ID NO. 12)
5' CGACGAAGCGCAGACAGCGUC UUCAAGAGA GACGCUGUCUGCGCUUCGUCG 3'

REFERENCES

1. Alexander M R and Owens G K. Epigenetic control of smooth muscle cell differentiation and phenotypic switching in vascular development and disease. *Annu Rev Physiol* 74: 13-40, 2012.
2. Asosingh K, Aldred M A, Vasanji A, Drazba J, Sharp J, Farver C, Comhair S A, Xu W, Licina L, Huang L, Anand-Apte B, Yoder M C, Tuder R M, and Erzurum S C. Circulating angiogenic precursors in idiopathic pulmonary arterial hypertension. *The American journal of pathology* 172: 615-627, 2008.
3. Ata H, Rawat D K, Lincoln T, and Gupte S A. Mechanism of glucose-6-phosphate dehydrogenase-mediated regulation of coronary artery contractility. *Am J Physiol Heart Circ Physiol* 300: H2054-2063, 2011.
4. Bouchier-Hayes L, Oberst A, McStay G P, Connell S, Tait S W, Dillon C P, Flanagan J M, Beere H M, and Green D R. Characterization of cytoplasmic caspase-2 activation by induced proximity. *Mol Cell* 35: 830-840, 2009.
5. Buchakjian M R and Kornbluth S. The engine driving the ship: metabolic steering of cell proliferation and death. *Nat Rev Mol Cell Biol* 11: 715-727, 2010.
6. Bull T M, Coldren C D, Geraci M W, and Voelkel N F. Gene expression profiling in pulmonary hypertension. *Proc Am Thorac Soc* 4: 117-120, 2007.
7. Cai T, Kuang Y, Zhang C, Zhang Z, Chen L, Li B, Li Y, Wang Y, Yang H, Han Q, and Zhu Y. Glucose-6-phosphate dehydrogenase and NADPH oxidase 4 control STAT5 activity in melanoma cells through a pathway involving reactive oxygen species, c-SRC and SHP2. *Am J Cancer Res* 5: 1610-1620, 2015.
8. Campbell G R and Campbell J H. Smooth muscle phenotypic changes in arterial wall homeostasis: implications for the pathogenesis of atherosclerosis. *Exp Mol Pathol* 42: 139-162, 1985.
9. Campbell J H and Campbell G R. Smooth muscle phenotypic modulation—a personal experience. *Arteriosclerosis, thrombosis, and vascular biology* 32: 1784-1789, 2012.
10. Chettimada S, Gupte R, Rawat D, Gebb S A, McMurtry I F, and Gupte S A. Hypoxia-induced glucose-6-phosphate dehydrogenase overexpression and -activation in pulmonary artery smooth muscle cells: implication in pulmonary hypertension. *American journal of physiology Lung cellular and molecular physiology* 308: L287-300, 2015.
11. Chettimada S, Joshi S R, Alzoubi A, Gebb S A, McMurtry I F, Gupte R, and Gupte S A. Glucose-6-phosphate dehydrogenase plays a critical role in hypoxia-induced CD133+ progenitor cells self-renewal and stimulates their accumulation in the lungs of pulmonary hypertensive rats. *American journal of physiology Lung cellular and molecular physiology* 307: L545-556, 2014.
12. Chettimada S, Rawat D K, Dey N, Kobelja R, Simms Z, Wolin M S, Lincoln T M, and Gupte S A. Glc-6-PD and PKG contribute to hypoxia-induced decrease in smooth muscle cell contractile phenotype proteins in pulmonary artery. *American journal of physiology Lung cellular and molecular physiology* 303: L64-74, 2012.
13. Gupte S A. Glucose-6-phosphate dehydrogenase: a novel therapeutic target in cardiovascular diseases. *Curr Opin Investig Drugs* 9: 993-1000, 2008.
14. Gupte S A and Wolin M S. Relationships between vascular oxygen sensing mechanisms and hypertensive disease processes. *Hypertension* 60: 269-275, 2012.
15. Joshi S R, Corner B S, McLendon J M, and Gerthoffer W T. MicroRNA Regulation of Smooth Muscle Phenotype. *Molecular and cellular pharmacology* 4: 1-16, 2012.
16. Leopold J A, Walker J, Scribner A W, Voetsch B, Zhang Y Y, Loscalzo A J, Stanton R C, and Loscalzo J. Glucose-6-phosphate dehydrogenase modulates vascular endothelial growth factor-mediated angiogenesis. *J Biol Chem* 278: 32100-32106, 2003.
17. Nutt L K, Margolis S S, Jensen M, Herman C E, Dunphy W G, Rathmell J C, and Kornbluth S. Metabolic regulation of oocyte cell death through the CaMKII-mediated phosphorylation of caspase-2. *Cell* 123: 89-103, 2005.
18. Owens G K, Kumar M S, and Wamhoff B R. Molecular regulation of vascular smooth muscle cell differentiation in development and disease. *Physiological reviews* 84: 767-801, 2004.
19. Wang X, Liu H, Zhang X, Li X, Gu H, Zhang H, and Fan R. G6PD downregulation triggered growth inhibition and induced apoptosis by regulating STAT3 signaling pathway in esophageal squamous cell carcinoma. *Tumour Biol* 37: 781-789, 2016.

Many modifications and variations of this invention can be made without departing from its spirit and scope, as will be apparent to those skilled in the art. The invention is defined by the terms of the appended claims, along with the full scope of equivalents to which such claims are entitled. The specific embodiments described herein, including the following examples, are offered by way of example only, and do not by their details limit the scope of the invention.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. The foregoing written specification is considered to be sufficient to enable one skilled in the art to practice the invention. Various modifications of the invention in addition to those shown and described herein will become apparent to those skilled in the art from the foregoing description and fall within the scope of the appended claims.

What is claimed is:

1. A method for treating a cardiovascular disorder and/or a pulmonary disorder in a subject in need thereof, comprising administering to the subject a therapeutically effective amount of a polynucleotide inhibitor of Glucose-6-phosphate dehydrogenase (G6PD) or a nucleic acid encoding G6PD, wherein the polynucleotide inhibitor comprises the nucleotide sequence set forth in SEQ ID NO:4, SEQ ID NO:5, SEQ ID NO:6, SEQ ID NO:7, SEQ ID NO:9, SEQ ID NO:10, SEQ ID NO:11, SEQ ID NO:12, or combinations thereof.

2. The method of claim 1, wherein the polynucleotide inhibitor comprises an RNA interference (RNAi) inhibitor.

3. The method of claim 1, wherein the polynucleotide inhibitor comprises a small interfering RNA (siRNA), a short hairpin RNA (shRNA), or a combination thereof.

4. The method of claim 1, wherein the polynucleotide inhibitor comprises an antisense oligonucleotide targeting a nucleic acid encoding G6PD.

5. The method of claim 1, wherein the cardiovascular disorder comprises pulmonary hypertension, pulmonary hypertension-associated heart failure, cardiomyopathy, hypertension, stroke, ischemic cardiomyopathy, medial hypertrophy, acute neointimal formation following iatrogenic interventions, atherosclerosis, congestive heart failure, or combinations thereof.

6. The method of claim 1, wherein the cardiovascular disorder and/or a pulmonary disorder comprises angiosarcoma, hemangioscarcoma, Timothy Syndrome, hypertrophic cardiomyopathy, atrial fibrillation, or combinations thereof.

7. The method of claim 1, wherein the cardiovascular disorder and/or pulmonary disorder comprises any of the groups of pulmonary hypertension 1-5, or combinations thereof.

8. The method of claim 7, wherein the disorder comprises scleroderma, categorized as pulmonary hypertension group I.

9. The method of claim 1, further comprising treating the subject with a diuretic, a vasodilator, an inotropic agent, an angiotensin converting enzyme (ACE) inhibitor, a beta blocker, a neurohumoral blocker, an aldosterone antagonist, a histone deacetylase inhibitor, erythropoietin, or combinations thereof.

10. The method of claim 1, further comprising treating the subject with a medical device and/or surgery.

11. The method of claim 10, wherein the medical device comprises a bi-ventricular pacemaker, an implantable cardioverter-defibrillator (ICD), a ventricular assist device (VAD), a left ventricular assist device (LVAD), a cardiac resynchronization therapy (CRT), or combinations thereof.

12. A method of treating a cardiovascular disorder and/or a pulmonary disorder in a subject in need thereof, comprising administering a composition comprising a polynucleotide inhibitor of Glucose-6-phosphate dehydrogenase (G6PD) or a nucleic acid encoding G6PD, wherein the polynucleotide inhibitor comprises the nucleotide sequence set forth in SEQ ID NO:4, SEQ ID NO:5, SEQ ID NO:6, SEQ ID NO:7, SEQ ID NO:9, SEQ ID NO:10, SEQ ID NO:11, SEQ ID NO:12, or combinations thereof to the subject.

* * * * *

SEQUENCE LISTING

<160> NUMBER OF SEQ ID NOS: 12

<210> SEQ ID NO 1
<211> LENGTH: 1638
<212> TYPE: DNA
<213> ORGANISM: Human

<400> SEQUENCE: 1

| | | | | | |
|---|---|---|---|---|---|
| atgggccggc | ggggctcagc | ccccggaaac | ggtcgtacac | ttcggggctg | cgagcgcgga | 60 |
| gggcgacgac | gacgaagcgc | agacagcgtc | atggcagagc | aggtggccct | gagccggacc | 120 |
| caggtgtgcg | ggatcctgcg | ggaagagctt | ttccagggcg | atgccttcca | tcagtcggat | 180 |
| acacacatat | tcatcatcat | gggtgcatcg | ggtgacctgg | ccaagaagaa | gatctacccc | 240 |
| accatctggt | ggctgttccg | ggatggcctt | ctgcccgaaa | acaccttcat | cgtgggctat | 300 |
| gcccgttccc | gcctcacagt | ggctgacatc | cgcaaacaga | gtgagccctt | cttcaaggcc | 360 |
| accccagagg | agaagctcaa | gctggaggac | ttctttgccc | gcaactccta | tgtggctggc | 420 |
| cagtacgatg | atgcagcctc | ctaccagcgc | ctcaacagcc | acatgaatgc | cctccacctg | 480 |
| gggtcacagg | ccaaccgcct | cttctacctg | gccttgcccc | cgaccgtcta | cgaggccgtc | 540 |
| accaagaaca | ttcacgagtc | ctgcatgagc | cagataggct | ggaaccgcat | catcgtggag | 600 |
| aagcccttcg | ggagggacct | gcagagctct | gaccggctgt | ccaaccacat | ctcctccctg | 660 |
| ttccgtgagg | accagatcta | ccgcatcgac | cactacctgg | gcaaggagat | ggtgcagaac | 720 |
| ctcatggtgc | tgagatttgc | caacaggatc | ttcggcccca | tctggaaccg | ggacaacatc | 780 |
| gcctgcgtta | tcctcacctt | caaggagccc | tttggcactg | agggtcgcgg | gggctatttc | 840 |
| gatgaatttg | ggatcatccg | ggacgtgatg | cagaaccacc | tactgcagat | gctgtgtctg | 900 |
| gtggccatgg | agaagcccgc | ctccaccaac | tcagatgacg | tccgtgatga | aaggtcaag | 960 |
| gtgttgaaat | gcatctcaga | ggtgcaggcc | aacaatgtgg | tcctgggcca | gtacgtgggg | 1020 |
| aaccccgatg | gagagggcga | ggccaccaaa | gggtacctgg | acgacccac | ggtgccccgc | 1080 |
| gggtccacca | ccgccacttt | tgcagccgtc | gtcctctatg | tggagaatga | gaggtgggat | 1140 |
| ggggtgccct | tcatcctgcg | ctgcggcaag | gccctgaacg | agcgcaaggc | cgaggtgagg | 1200 |
| ctgcagttcc | atgatgtggc | cggcgacatc | ttccaccagc | agtgcaagcg | caacgagctg | 1260 |
| gtgatccgcg | tgcagcccaa | cgaggccgtg | tacaccaaga | tgatgaccaa | gaagccgggc | 1320 |
| atgttcttca | accccgagga | gtcggagctg | gacctgacct | acggcaacag | atacaagaac | 1380 |
| gtgaagctcc | ctgacgccta | cgagcgcctc | atcctggacg | tcttctgcgg | gagccagatg | 1440 |
| cacttcgtgc | gcagcgacga | gctccgtgag | gcctggcgta | ttttcacccc | actgctgcac | 1500 |
| cagattgagc | tggagaagcc | caagcccatc | ccctatattt | atggcagccg | aggccccacg | 1560 |
| gaggcagacg | agctgatgaa | gagagtgggt | ttccagtatg | agggcaccta | caagtgggtg | 1620 |
| aaccccccaca | agctctga | | | | 1638 |

<210> SEQ ID NO 2

-continued

```
<211> LENGTH: 19
<212> TYPE: RNA
<213> ORGANISM: Artificial Sequence
<220> FEATURE:
<223> OTHER INFORMATION: Synthetic

<400> SEQUENCE: 2
caacaucgcc ugcguuauc                                                   19

<210> SEQ ID NO 3
<211> LENGTH: 90
<212> TYPE: DNA
<213> ORGANISM: Human

<400> SEQUENCE: 3
atgggccggc ggggctcagc ccccggaaac ggtcgtacac ttcggggctg cgagcgcgga     60
gggcgacgac gacgaagcgc agacagcgtc                                      90

<210> SEQ ID NO 4
<211> LENGTH: 21
<212> TYPE: RNA
<213> ORGANISM: Artificial Sequence
<220> FEATURE:
<223> OTHER INFORMATION: Synthetic

<400> SEQUENCE: 4
cggaaacggu cguacacuuc g                                                21

<210> SEQ ID NO 5
<211> LENGTH: 21
<212> TYPE: RNA
<213> ORGANISM: Artificial Sequence
<220> FEATURE:
<223> OTHER INFORMATION: Synthetic

<400> SEQUENCE: 5
cgaaguguac gaccguuucc g                                                21

<210> SEQ ID NO 6
<211> LENGTH: 21
<212> TYPE: RNA
<213> ORGANISM: Artificial Sequence
<220> FEATURE:
<223> OTHER INFORMATION: Synthetic

<400> SEQUENCE: 6
cgacgaagcg cagacagcgu c                                                21

<210> SEQ ID NO 7
<211> LENGTH: 21
<212> TYPE: RNA
<213> ORGANISM: Artificial Sequence
<220> FEATURE:
<223> OTHER INFORMATION: Synthetic

<400> SEQUENCE: 7
gacgcugucu gcgcuucguc g                                                21

<210> SEQ ID NO 8
<211> LENGTH: 9
<212> TYPE: RNA
<213> ORGANISM: Artificial Sequence
<220> FEATURE:
<223> OTHER INFORMATION: Synthetic

<400> SEQUENCE: 8
```

```
uucaagaga                                                                          9

<210> SEQ ID NO 9
<211> LENGTH: 51
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(30)
<223> OTHER INFORMATION: n is a, c, g, or u

<400> SEQUENCE: 9
cggaaacggu cguacacuuc gnnnnnnnnn cgaaguguac gaccguuucc g         51

<210> SEQ ID NO 10
<211> LENGTH: 51
<212> TYPE: RNA
<213> ORGANISM: Artificial Sequence
<220> FEATURE:
<223> OTHER INFORMATION: Synthetic

<400> SEQUENCE: 10
cggaaacggu cguacacuuc guucaagaga cgaaguguac gaccguuucc g         51

<210> SEQ ID NO 11
<211> LENGTH: 51
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (22)..(30)
<223> OTHER INFORMATION: n is a, c, g, or u

<400> SEQUENCE: 11
cgacgaagcg cagacagcgu cnnnnnnnnn gacgcugucu gcgcuucguc g         51

<210> SEQ ID NO 12
<211> LENGTH: 51
<212> TYPE: RNA
<213> ORGANISM: Artificial Sequence
<220> FEATURE:
<223> OTHER INFORMATION: Synthetic

<400> SEQUENCE: 12
cgacgaagcg cagacagcgu cuucaagaga gacgcugucu gcgcuucguc g         51
```